United States Patent
Izumi

(10) Patent No.: US 8,608,655 B2
(45) Date of Patent: Dec. 17, 2013

(54) SLEEP EVALUATION DEVICE

(75) Inventor: Shuichi Izumi, Tokyo (JP)

(73) Assignee: Tanita Corporation, Tokyo (JP)

( * ) Notice: Subject to any disclaimer, the term of this patent is extended or adjusted under 35 U.S.C. 154(b) by 136 days.

(21) Appl. No.: 12/134,881

(22) Filed: Jun. 6, 2008

(65) Prior Publication Data

US 2008/0306351 A1    Dec. 11, 2008

(30) Foreign Application Priority Data

Jun. 6, 2007  (JP) ................................ 2007-150646

(51) Int. Cl.
    *A61B 5/00*    (2006.01)
(52) U.S. Cl.
    USPC ............................ 600/301; 600/300; 702/189
(58) Field of Classification Search
    USPC .................... 600/300–301; 705/2–4; 702/189
    See application file for complete search history.

(56) References Cited

U.S. PATENT DOCUMENTS

| | | | |
|---|---|---|---|
| 6,519,545 B1* | 2/2003 | Amano | 702/127 |
| 6,805,668 B1* | 10/2004 | Cadwell | 600/300 |
| 6,826,575 B1* | 11/2004 | Waclawski | 1/1 |
| 6,988,056 B2* | 1/2006 | Cook | 702/189 |
| 7,207,938 B2* | 4/2007 | Hursh | 600/300 |
| 7,427,270 B2* | 9/2008 | Izumi et al. | 600/534 |
| 7,640,055 B2* | 12/2009 | Geva et al. | 600/544 |
| 2003/0149678 A1* | 8/2003 | Cook | 706/46 |
| 2004/0193064 A1* | 9/2004 | Shusterman | 600/504 |
| 2004/0220782 A1* | 11/2004 | Cook | 702/189 |
| 2005/0042589 A1* | 2/2005 | Hatlestad et al. | 434/262 |
| 2006/0009704 A1 | 1/2006 | Okada et al. | |
| 2006/0085497 A1* | 4/2006 | Sehitoglu | 708/405 |
| 2006/0169282 A1 | 8/2006 | Izumi et al. | 128/204.23 |
| 2006/0177837 A1* | 8/2006 | Borozan et al. | 435/6 |
| 2006/0241359 A1 | 10/2006 | Nagai et al. | |
| 2006/0253044 A1* | 11/2006 | Zhang et al. | 600/512 |
| 2006/0253164 A1* | 11/2006 | Zhang et al. | 607/28 |
| 2006/0293608 A1* | 12/2006 | Rothman et al. | 600/545 |
| 2007/0015976 A1* | 1/2007 | Miesel et al. | 600/301 |
| 2007/0016095 A1* | 1/2007 | Low et al. | 600/544 |
| 2007/0123758 A1 | 5/2007 | Miesel et al. | |
| 2007/0142733 A1* | 6/2007 | Hatlestad et al. | 600/508 |

(Continued)

FOREIGN PATENT DOCUMENTS

| | | |
|---|---|---|
| JP | 2001-061819 A | 3/2001 |
| JP | 2002-219116 | 8/2002 |

(Continued)

OTHER PUBLICATIONS

EP Search Report dated Oct. 30, 2009.

(Continued)

*Primary Examiner* — Bill Thomson
*Assistant Examiner* — Bobby Soriano
(74) *Attorney, Agent, or Firm* — Hogan Lovells US LLP

(57) ABSTRACT

A sleep evaluation device 1 is provided with a respiration detection unit 7 that detects changes in respiration and outputs respiration signals. CPU 6 generates six primary parameters indicating sleep states based on the respiration signals and four secondary parameters based on the primary parameters. The secondary parameters are linearly independent of one another. Evaluation unit 20 computes a sleep score indicating the degree of the quality of sleep by multiplying each of the four secondary parameters by second coefficients and totalizing results of the multiplications. Results of the evaluations are displayed on display unit 4.

13 Claims, 31 Drawing Sheets

(56) References Cited

U.S. PATENT DOCUMENTS

| | | | |
|---|---|---|---|
| 2007/0161873 A1* | 7/2007 | Ni et al. | 600/300 |
| 2007/0173705 A1* | 7/2007 | Teller et al. | 600/300 |
| 2007/0179357 A1* | 8/2007 | Bardy | 600/300 |
| 2009/0149778 A1* | 6/2009 | Naujokat et al. | 600/595 |

FOREIGN PATENT DOCUMENTS

| | | |
|---|---|---|
| JP | 2004-113618 A | 4/2004 |
| JP | 2006-280686 | 10/2006 |
| JP | 2006-296940 A | 11/2006 |
| JP | 2007-319238 A | 12/2007 |
| WO | 2006054306 A2 | 5/2006 |

OTHER PUBLICATIONS

Japanese Office Action, Japanese Patent Application No. 2007-150646, issued date Apr. 10, 2012.

* cited by examiner

SLEEP EVALUATION DEVICE

CROSS REFERENCE TO RELATED APPLICATIONS

This application claims priority under 35 U.S.C. §119 to Japanese Patent Application No. JP 2007-150646, filed Jun. 6, 2007, which application is expressly incorporated herein by reference in its entirety.

BACKGROUND OF THE INVENTION

1. Field of the Invention

The present invention relates to a device for evaluating the quality of sleep.

2. Description of Related Art

Conventionally, a test called polysomnography (PSG) has been performed at hospitals to detect sleep stages. In a PSG test, brain waves (in an electroencephalogram, EEG), eye movements (in an electrooculogram, EOG), and chin movements (in an electromyogram, or an EMG of mentalis muscles) are recorded as parameters for detecting the sleep stages. This test, however, requires cumbersome operations because the electrodes must be attached on the body of the person being examined while measurements of the parameters are taken. Furthermore, specialized knowledge or skills are required for the operations of the measurement devices. Thus, the PSG test is not a test that can be readily performed at home.

On the other hand, in Japanese Patent Application Laid-Open Publication No. 2002-219116, there is disclosed a device for detecting, by providing vibration sensors such as piezoelectric elements under bedding, at least one of large movements (gross movements) and heart rate of a subject lying on the bedding, to compute the frequency of large movements or heart rate fluctuation based on the detected data and for determining sleep stages based on correlation between sleep cycles and the computed data. In Japanese Patent Application Laid-Open Publication No. 2006-280686, there is disclosed a device in which sleep stages are detected based on breathing activity so that the detection can be made more precisely.

The conventional devices, however, merely allow detection of the sleep stages, and it was not able to evaluate the degree of quality of sleep in a comprehensive manner.

SUMMARY OF INVENTION

The present invention was made in consideration of the above, and the present invention has as an object to provide a sleep evaluation device that is provided with a biometric (biological) signal measurer that measures a state of a human subject, for output as a biometric signal; a primary parameter generator that generates, based on the biometric signal, n number of primary parameters indicating a state of sleep, the n being a natural number that is at least 2; a secondary parameter generator that generates m number of secondary parameters by multiplying each of the n number of primary parameters by an eigenvector as a first coefficient and totalizing results of the multiplications, the m being a natural number satisfying n≥m and a correlation coefficient of any two of the secondary parameters being smaller than a correlation coefficient of any two of the primary parameters; and a sleep index generator that computes a sleep index indicating a quality of sleep based on a result of computation obtained by multiplying each of the secondary parameters by a second coefficient and totalizing results of the multiplications. Preferably, the sleep score may be computed by performing the four fundamental operations of arithmetic on the result of the above computation. For example, the result of the computation may be multiplied by a first constant. Alternatively, a second constant may be added to the product of the first constant and the result of the computation.

In the invention, a correlation coefficient between any two of the m number of the secondary parameters is smaller a correlation coefficient between any two of the n number of primary parameters. Therefore, the m number of secondary parameters is better suited for accurately indicating a state of sleep of a subject than the primary parameters are. Thus, according to the sleep evaluation device of the present invention, the quality of the sleep can be accurately evaluated.

Preferably, the first coefficient may be set so that the m number of secondary parameters is linearly independent. Furthermore, the second coefficient is preferably a value obtained by multiplying the first coefficient by the square root of an eigenvalue. The second coefficient therefore is treated as a factor loading, which in turn makes the value of the second coefficient a coefficient value dependent on the degree at which the secondary parameter affects the quality of sleep.

In a preferred embodiment, the primary parameter generator may generate, based on the biometric signals, as the n number of primary parameters, at least three states: sleep latency, sleep efficiency, mid-arousal number, deep sleep latency, deep sleep time, movement number, total bed time, out-of-bed latency, sleep time, total sleep time, mid-arousal period, REM sleep latency, light sleep period, REM sleep period, sleep stage change number, light sleep occurrence number, REM sleep occurrence number, deep sleep occurrence number, REM sleep duration, REM sleep interval, REM sleep cycle, sleep cycle, ratio of light sleep in the first half and the second half of sleep, the ratio of REM sleep in the first half and the second half of sleep, and the ratio of deep sleep in the first half and the second half of sleep.

Furthermore, the primary parameter generator may preferably generate, as the n number of primary parameters, the sleep latency, the mid-arousal number, the deep sleep latency, the deep sleep time, and the movement number; and the secondary parameter generator may select, as the m number of secondary parameters, four secondary parameters. In this case, the number of parameters is aggregated and reduced to four.

In another preferred embodiment, the sleep evaluation device may be further provided with an inputter for receiving an input of characteristics data of the human subject being examined, and the primary parameter generator may store a plurality of the first coefficients, each corresponding to each of plural groups of populations categorized in accordance with the characteristics of human subjects, and compute the primary parameters using the first coefficients corresponding to the characteristics received by the inputter; and the secondary parameter generator may store a plurality of the second coefficients, each corresponding to each of plural groups of populations categorized in accordance with the characteristics of human subjects and computes the secondary parameters using the second coefficients corresponding to the characteristics received by the inputter. The value of parameters such as sleep time and sleep latency should vary depending on the characteristics of a human subject, such as the age and sex. On the other hand, the first coefficients and the second coefficients are generated based on a certain population group. Therefore, by selecting a population group depending on the characteristics of the subject being examined, the quality of the sleep can be more accurately measured.

In still another preferred embodiment of the present invention, the biometric signal measurer may measure the changes in respiration of a human subject and output respiration signals as biometric signals. Body movements and respiratory rates are reflected in the respiration signals. Therefore, by extracting the body movements and respiratory rates from the respiration signals, stages of sleep can be determined, which in turn enables the generation of various primary parameters. Preferably, the biometric signal measurer may be provided with a heart rate detector capable of detecting heart rates, and respiratory rates may be modified by the detected heart rates. For example, in a case in which the subject being examined is suffering from a sleep disorder called "sleep apnea", characterized by pauses in breathing during sleep, respiration signals are sometimes not detected in succession. In such a case, the detected heart rates can be used to modify results of determinations on the sleep stages, thereby providing more accurate index on the quality of sleep.

BRIEF DESCRIPTION OF THE DRAWINGS

With reference to the accompanying drawings, various embodiments of the present invention will be described hereinafter. In the drawings.

DETAILED DESCRIPTION OF PREFERRED EMBODIMENTS

A sleep evaluation device according to an embodiment of the present invention is capable of detecting breathing activity, determining sleep stages, and evaluating the quality of sleep based on the determinations. In the following, description will be given of the sleep evaluation device with reference to the attached drawings.

Figure 1:
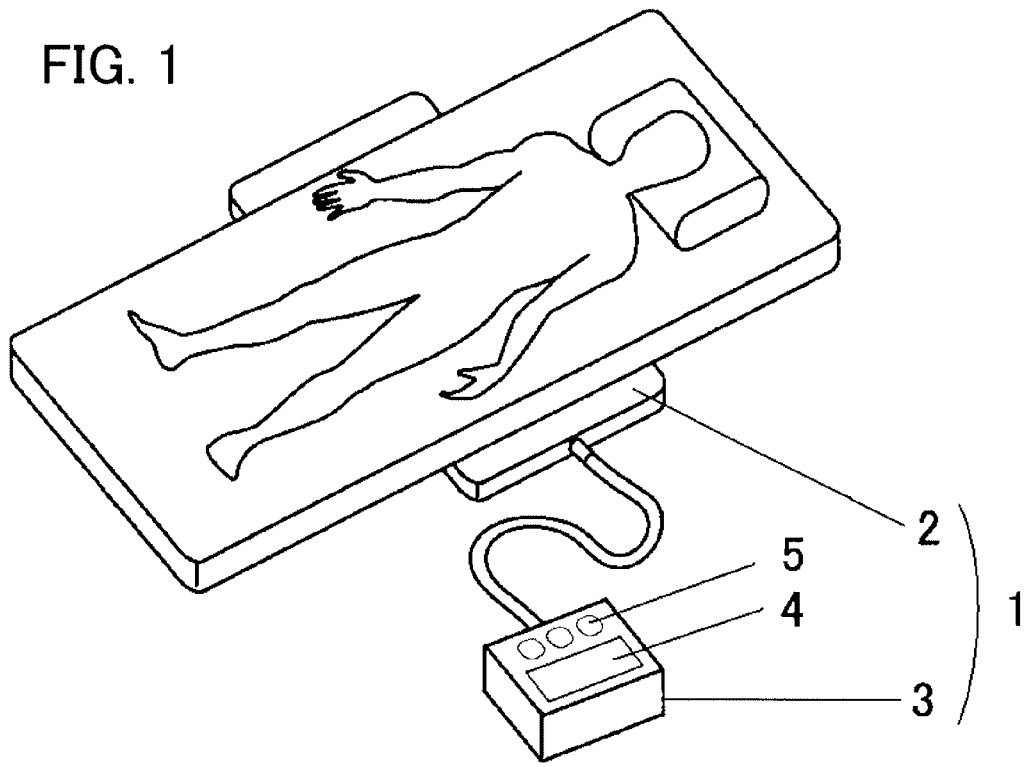
FIG. 1 is a perspective view of sleep evaluation device 1 when the device is being used.
Figure 2:
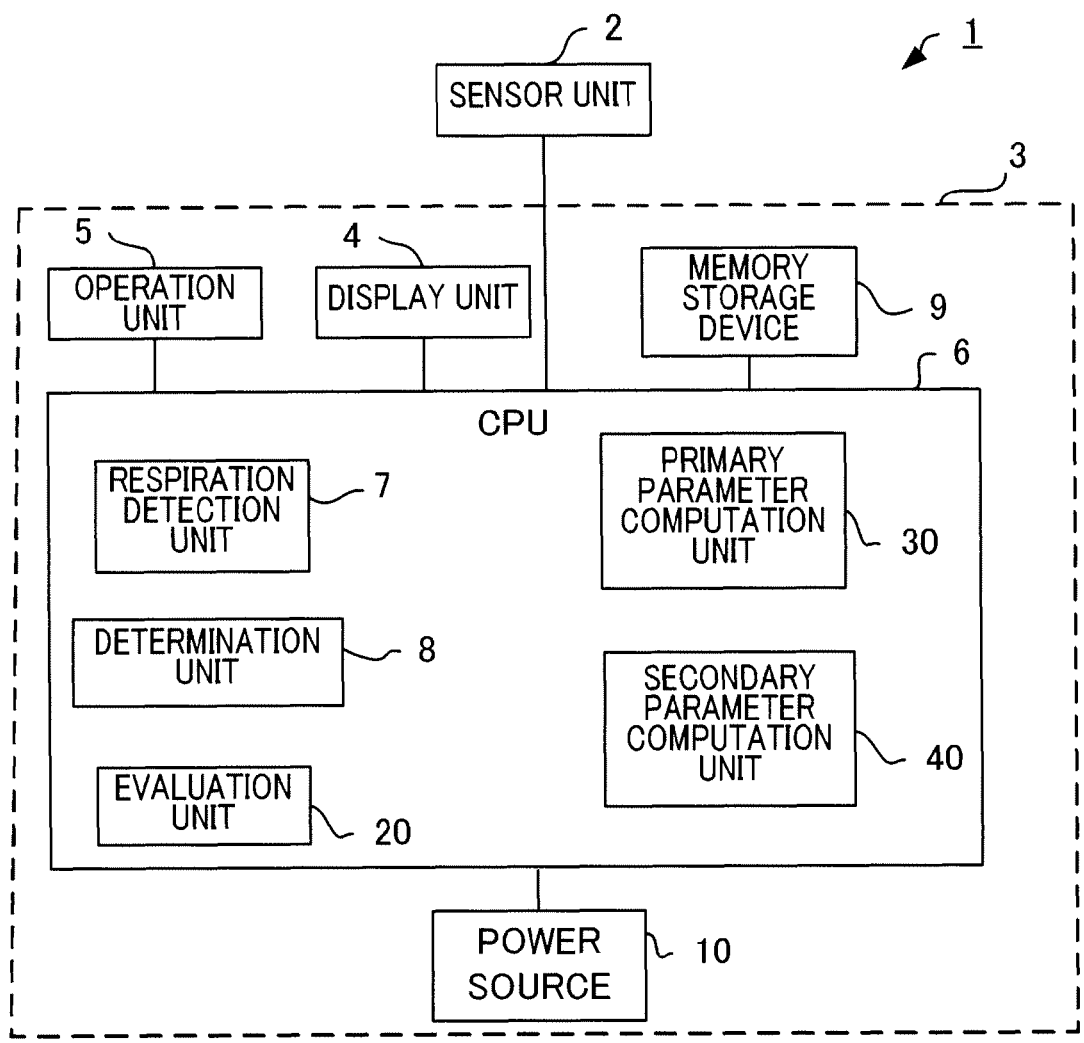
FIG. 2 is a block diagram showing a configuration of sleep evaluation device 1.

FIGS. 1 and 2 will be first referred to, to describe a configuration of a sleep evaluation device 1 of present embodiment. FIG. 1 is a perspective view of sleep evaluation device 1 when the device is being used. FIG. 2 is a block diagram showing a configuration of sleep evaluation device 1. In FIG. 1, sleep evaluation device 1 has a sensor unit 2 for detecting biometric signals of a human subject lying on the bedding and a control console 3 that is connected to sensor unit 2 and that determines the sleep stages and evaluates the quality of the sleep. Control console 3 includes a display unit 4 for displaying the result of the determination of the sleep stages and also for displaying guidance such as showing evaluation indices of the sleep. Control console 3 also includes an operation unit 5 for performing operations such as power-on or power-off operations and measurement-start or measurement-ending operations.

Sensor unit 2 is, for example, capable of detecting, through a microphone (for example, a condenser microphone), variations in the pressure on a mattress in which an incompressible fluid is sealed. As shown in the figure, the mattress is spread under the bedding, so that sensor unit 2 detects biometric signals including respiration signals or the changes in posture of a human subject who is lying on the bedding.

As shown in FIG. 2, in control console 3, there are provided sensor unit 2, display unit 4, and operation unit 5, a memory storage device 9, and a power source 10, each being connected to a CPU 6. Memory storage device 9 stores various conditional associations for the determination of the sleep stages and for the evaluation of the sleep and also stores results of the determinations and computations. Power source 10 supplies electric power to sleep evaluation device 1.

CPU 6 includes a respiration detection unit 7 that detects respiratory signals from biometric signals detected by sensor unit 2, a determination unit 8 that performs the determination of the sleep stages and various types of determinations and computation for the evaluation of the sleep, and an evaluator 20 that evaluates the quality of sleep. In this case, CPU 6 has provided therein a controller that controls sleep evaluation device 1 and a time keeper that measures time, and determination unit 8 includes the following eight determiners for determining the sleep stages: an in-bed or out-of-bed determiner 11, a body movement determiner 12, an arousal determiner 13, a sleep-onset period determiner 14, a deep sleep period determiner 15, a REM (Rapid Eye Movement) or light sleep determiner 16, a mid-arousal determiner 17, and a wake-up (or awoken) determiner 18 (not shown). In the present embodiment, the sleep stages determined by each determiner include the following four stages: an aroused stage, a deep sleep stage, a light sleep stage, and a REM sleep stage. Description of the above eight determiners will be given later by referring to corresponding flowcharts.

Furthermore, CPU 6 has a primary parameter computation unit 30 for computing primary parameters of sleep and a secondary parameter computation unit 40 for computing secondary parameters of sleep based on the results of computation performed by the primary parameter computation unit 30. In the present embodiment, "sleep latency or sleep onset latency (SL)", "sleep efficiency (SE)", "number of mid-arousals (WN)", "deep sleep latency (DL)", "deep sleep time (DT)", "number of movements or number of times the subject rolled over in bed (MN)" are computed as primary parameters, and "efficiency (Efficiency)", "sleep latency (Latency) ", "mid-arousals (Wake)", and "movements (Move) (e.g., rolling over)" are computed as secondary parameters. Therefore, determination unit 8 has, as primary parameter computation unit 30, a sleep latency computer, a sleep efficiency computer, a mid-arousal number computer, a deep sleep latency computer, a deep sleep time computer, and a movement number computer and has, as secondary parameter computation unit 40, an efficiency score computer, a sleep latency score computer, a mid-arousal score computer, and a movement score computer (not shown).

Evaluation unit 20 computes, based on the scores (principal component scores) of each parameter computed by secondary parameter computation unit 40, a comprehensive sleep score and displays on display unit 4 results of the evaluation.

The processes performed by evaluation unit 20, each of the parameter computers 30 and 40 will be described later with reference to flowcharts. Respiration detection unit 7, determination unit 8, evaluation unit 20, primary parameter computation unit 30, and secondary parameter computation unit 40 each performs the process shown in the corresponding flowchart by having CPU 6 execute a predetermined program. Accordingly, each of in-bed or out-of-bed determiner 11, body movement determiner 12, arousal determiner 13, sleep-onset period determiner 14, deep sleep period determiner 15, REM (Rapid Eye Movement) or light sleep determiner 16, mid-arousal determiner 17, and an awoken period determiner 18 of determination unit 8 performs the process, as shown in the corresponding flowchart, by having CPU 6 execute a predetermined program.

However, alternatively, independent CPUs may be provided for each of respiration detection unit 7, determination unit 8, evaluation unit 20, primary parameter computation unit 30, and secondary parameter computation unit 40.

Figure 3:
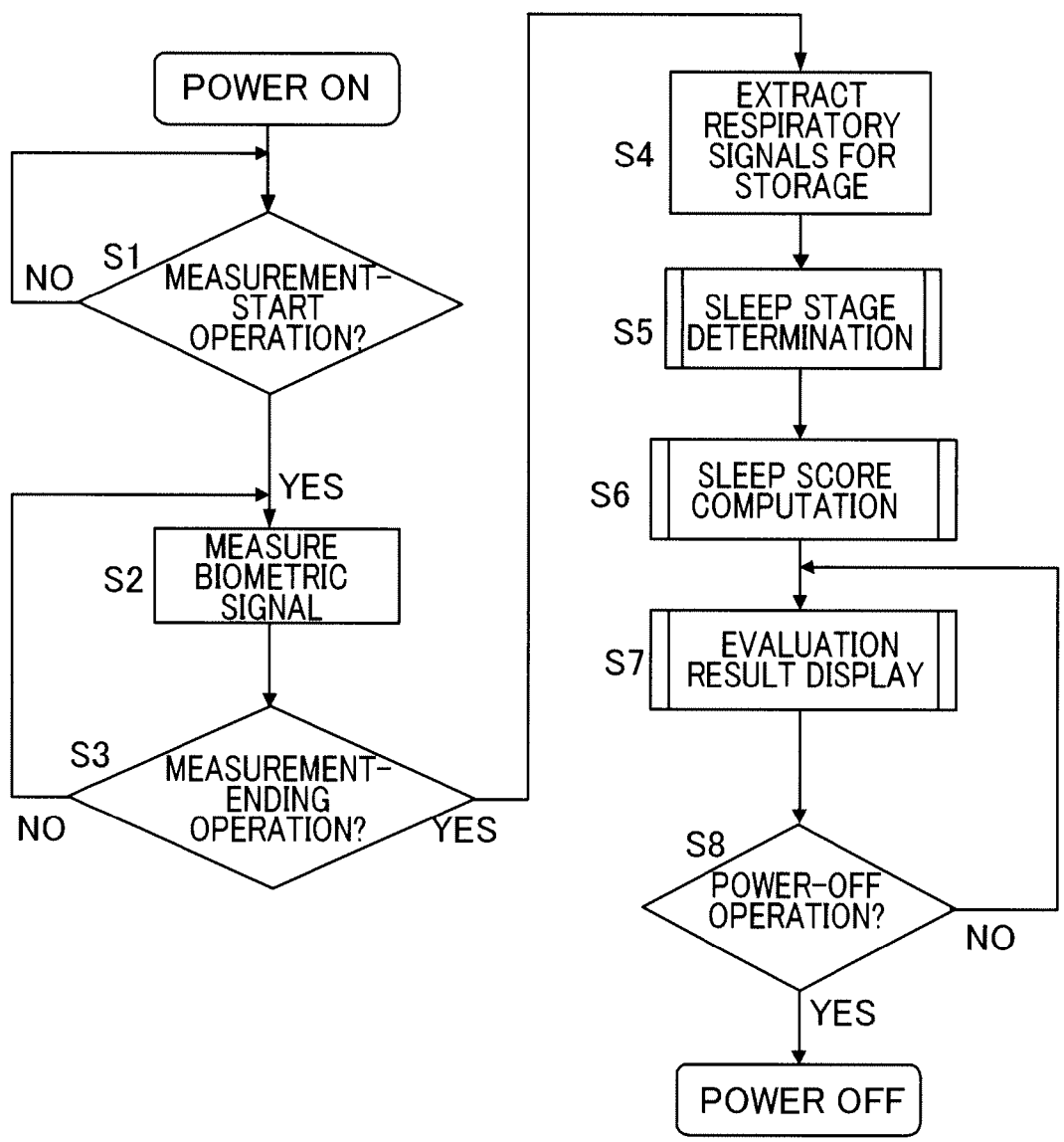
FIG. 3 is a flowchart showing a main operation.
Figure 4:
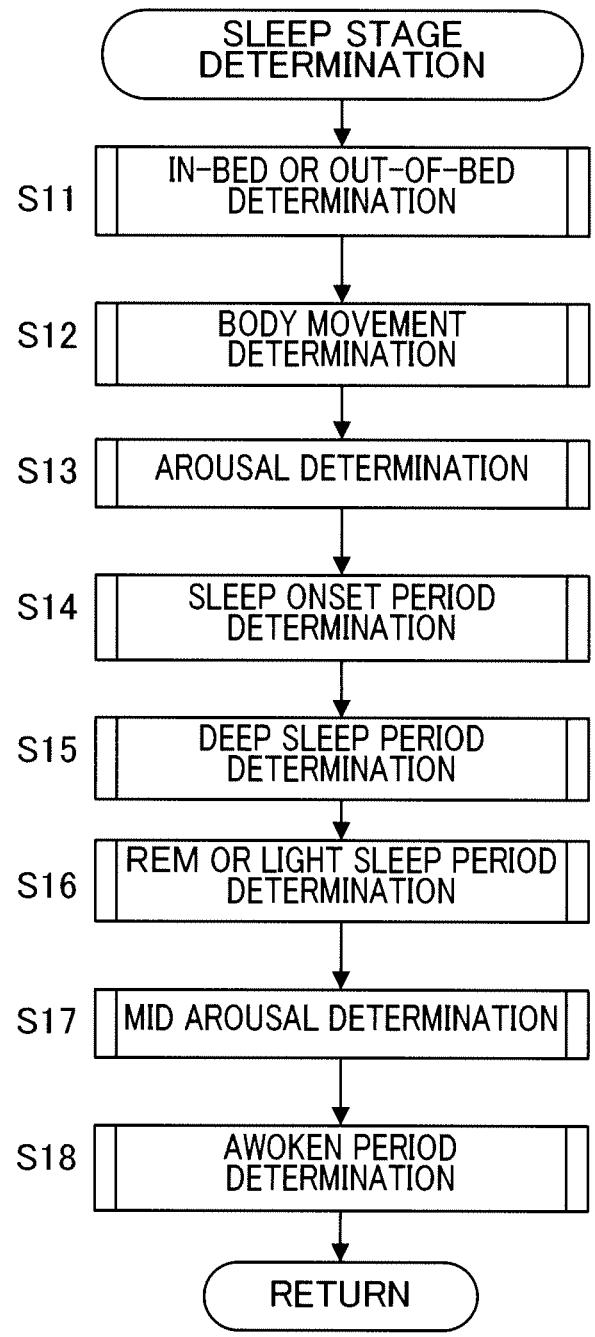
FIG. 4 is a flowchart showing a flow of a sleep stage determination process.

Description will be next given of a main operation of sleep evaluation device 1 with reference to the flowcharts shown in FIGS. 3 and 4. FIG. 3 is a flowchart showing the main operation, and FIG. 4 is a flowchart showing a flow of a sleep stage determination process performed by determiners 11 to 18.

As shown in FIG. 3, when the power of sleep evaluation device 1 is turned on by a power-on operation of operation unit 5, a guidance message is displayed in Step S1, the message prompting a user to lie down and to perform a measurement start operation of operation unit 5. In Step S1, it is then determined whether the measurement start operation has been performed. In a case in which no measurement start operation is performed, the determination changes to NO, and the guidance message remains displayed on the screen. In a case in which the measurement start operation is performed, the determination changes to YES, and in Step S2, biometric signals are detected by sensor unit 2 and stored in memory storage device 9 as biometric signal data together with data of a current time measured by the time keeping unit provided in CPU 6.

In Step S3, it is determined whether an operation for ending the measurement has been performed. In a case in which no measurement ending operation is performed, the determination changes to NO, and CPU 6 continues to perform detecting and storing of biometric signals of Step S2. On the other hand, in a case in which the measurement ending operation is performed, the determination changes to YES, and the controller of CPU 6 controls each unit to process the detected biometric signals in Step S4. That is, the controller reads the biometric signal data stored in the memory storage device 9, and the respiration detection unit 7 detects respiratory signals from the read data, so that the amplitudes and cycles of waveforms are computed based on the respiratory signals and stored as respiratory data in memory storage device 9. The respiratory data is stored for each predetermined period of time (for a unit period of, for example, 30 seconds, and the unit period will be hereinafter referred to as an "epoch"). Description will be omitted of the computation of the amplitude and cycle of waves since this technique is known. The duration of an epoch is not limited to 30 seconds and may be set to an arbitrary value so long as the precision of determination is not undermined.

In a case in which the respiratory data is detected and stored for all biometric data units stored in memory storage device 9, in Step S5, determiners 11 to 18 of determination unit 8 perform a sleep stage determination process (described later) based on the respiratory data.

In Step S6, CPU 6 performs a sleep score computation process that will be described later in detail. The sleep score is an index indicating a degree of the quality of sleep. In Step S7, an evaluation result display process is performed, in which the evaluation result is displayed on display unit 4. In Step S8, it is determined whether the power-off operation is performed. In a case in which no power-off operation is performed, the determination changes to NO, and what is displayed on display unit 4 in Step S7 remains on the screen. In a case in which the power-off operation is performed, the determination changes to YES. In this case, the power of sleep evaluation device 1 is turned off, and the process ends.

FIG. 4 is next referred to in describing a flow of the sleep stage evaluation performed by the determiners 11 to 18 of determination unit 8.

Determination unit 8 is controlled by CPU 6 and performs the following determination processes sequentially based on the respiratory data stored for each epoch in memory storage device 9 in Step S4 of FIG. 3.

Specifically, in each of the determination processes, in Step S11, in-bed or out-of-bed determiner 11 determines whether the subject being examined is in an in-bed or an out-of-bed state from the start to the end of the measurement based on changes in the respiratory data. In Step S12, body movement determiner 12 determines, based on the amplitude and cycle of waveforms obtained from the respiratory data, which of the following states each epoch is in: a large movement state, a slight movement state, and a state without movement. The large movements are large body movements such as rolling over, the slight movements are small body movements such as snoring, and the state without movement is when respiration is stable. In Step S13, arousal determiner 13 determines, depending on the determined state of movement, whether the subject being examined is in an obviously aroused state. In Step S14, sleep-onset period determiner 14 determines in which epoch a state transitions from an aroused state (full wakefulness) right after lying down to falling asleep (hereinafter referred to as a "sleep-onset period"). In Step S15, deep sleep period determiner 15 determines for each epoch, based on the changes in the respiratory data and the determined state of the body movement, whether the subject being examined is in a deep sleep state. In Step S16, REM/light sleep determiner 16 determines, for those epochs that were not determined as being in the deep sleep state in the previous step, whether the subject being examined is in the REM sleep state or in the light sleep state. In Step S17, mid-arousal determiner 17 determines, based on the length of duration of a body movement, whether there is any aroused state in the midst of the sleep state. In Step S18, awoken period determiner 18 determines in which epoch a state transitions from a sleep state to full wakefulness (will be referred to as a "awoken period").

After all the determinations are finished, the routine returns to the flowchart of FIG. 3 which shows the main operation. In Step S6, in the sleep score computation process, primary parameters are computed based on the results of the determinations performed by determination unit 8; and secondary parameters are computed based on the primary parameters. A sleep score is then computed based on the secondary parameters. In Step S7, the results of the evaluations are displayed on display unit 4, the results of the evaluations include the sleep score, a category (or a part) of the sleep score, the transition of sleep states during the sleep, and the transition of sleep scores.

Description will next be given sequentially of the processes performed by the determiners 11 to 18 with reference to the flowcharts shown in FIG. 5 to FIG. 16. In the following, constants represented by the alphabetical characters sometimes in combination with numerals are determined in advance based on correlation between the sleep stage determination according to the data obtained by the PSG test and data actually measured by sleep evaluation device 1.

Figure 5:
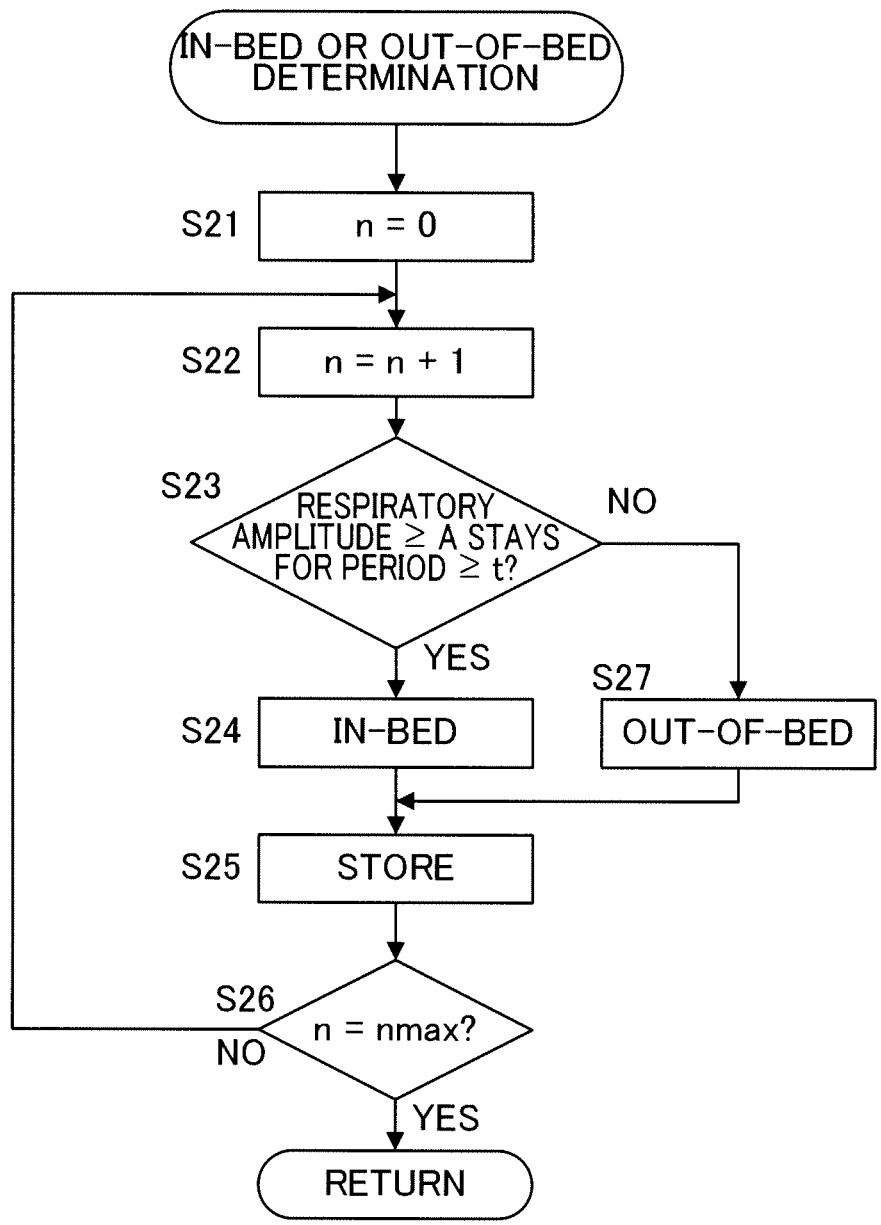
FIG. 5 is a flowchart showing a flow of an in-bed or out-of-bed determination process.
Figure 6:
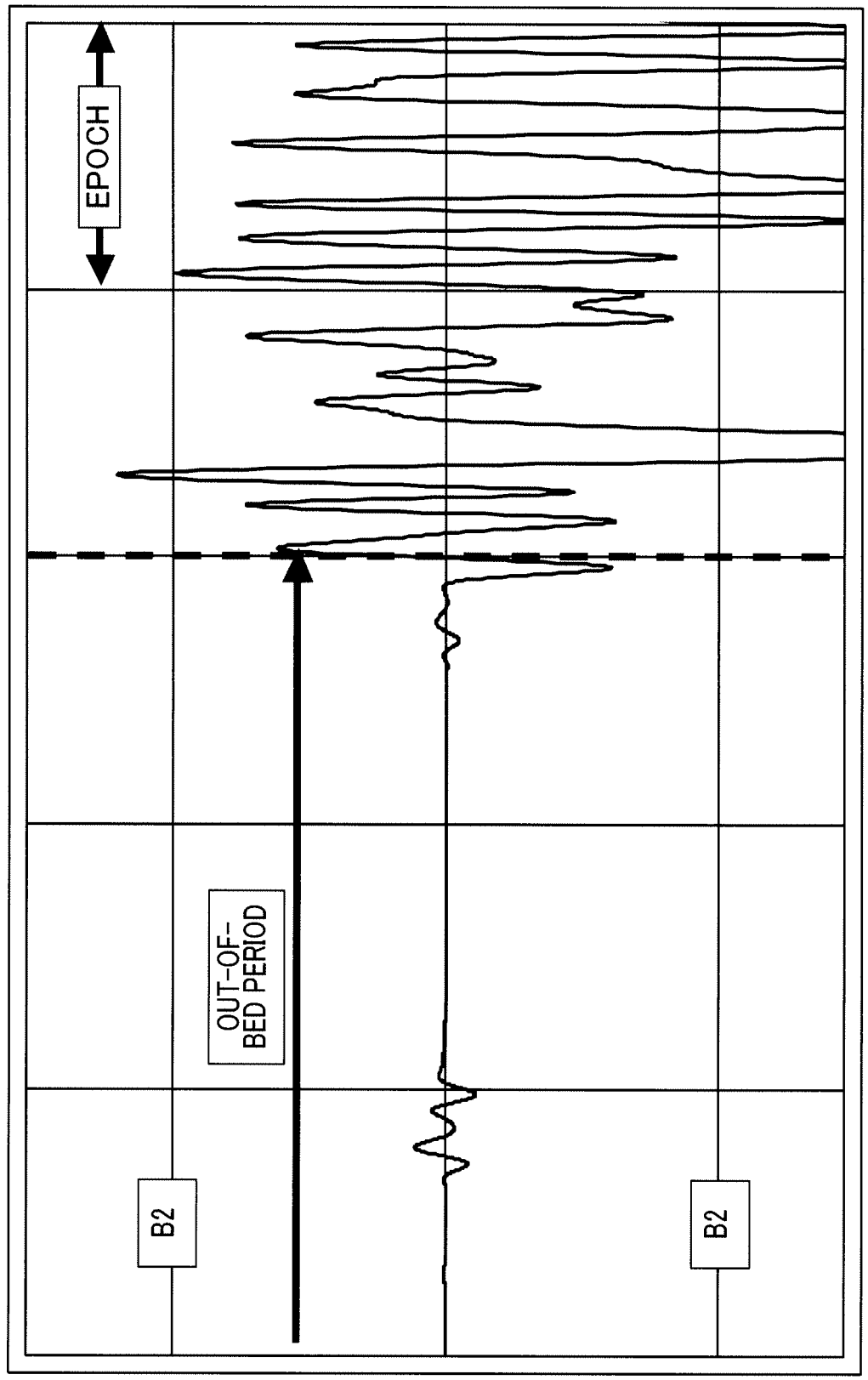
FIG. 6 is a flowchart showing respiration waveforms in an out-of-bed state.

FIG. 5 is now referred to, to describe the process performed by in-bed or out-of-bed determiner 11.

Provided that the total number of epochs is nmax and that the process is performed for each epoch from the n=1 interval to n=nmax interval, n is initially set as "n=0" in Step S21. Then in Step S22, the determiner 11 increments in epoch by one epoch with n=n+1 and reads the respiratory data corresponding to the subject epoch.

In Step S23, it is determined for an amplitude of each respiratory waveform in the epoch n whether a respiratory amplitude that is equal to or larger than A remains for a time period that is equal to or larger than t (sec) (see FIG. 6), where A is the minimum value of the amplitude in a case in which the subject being examined is in the face-up position; A and t are constants; and t is shorter than the duration of 1 unit period (i.e., epoch). If this is the case, the breathing activity is detected, and the determination of Step S23 changes to YES. In Step S24, it is determined that the subject epoch n is assigned an in-bed period because the subject being examined is in the bed. In Step S25, the result of the determination, i.e., data indicating the in-bed period, is stored in association with the subject epoch n in memory storage device 9. In a case in which the conditions of Step S23 are not fulfilled (Step S23 is NO), the breathing activity is not detected. In Step S27, the epoch n is assigned an out-of-bed period because the subject being examined is in an out-of-bed state. In Step S25, the result of the determination, i.e., data indicating the out-of-bed period, is stored in association with the subject epoch n in memory storage device 9. In Step S26, it is determined whether the in-bed or out-of-bed determination has been performed for all the epochs, i.e., it is determined whether n=nmax is true. In a case in which the in-bed or out-of-bed determination for all the epochs is not yet finished (Step S26 is NO), the routine returns to Step S22 in which n is incremented by 1 (n=n+1). In a case in which the in-bed or out-of-bed determination for all the epochs is finished, the determination of Step S26 changes to YES. The routine then returns to the flowchart of FIG. 4 and proceeds to the next determination.

Figure 7:
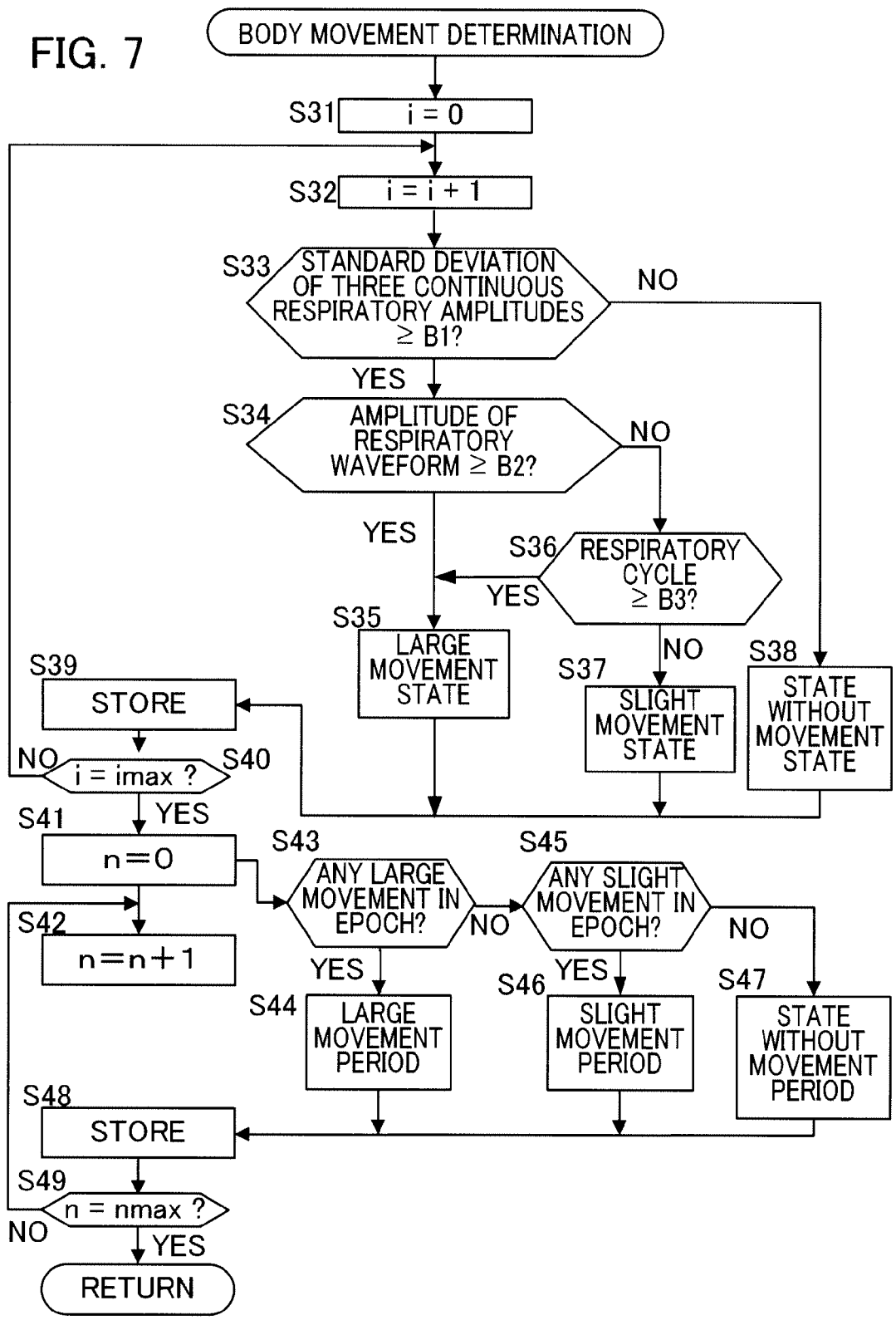
FIG. 7 is a flowchart showing a flow of a body movement determination process.
Figure 8:
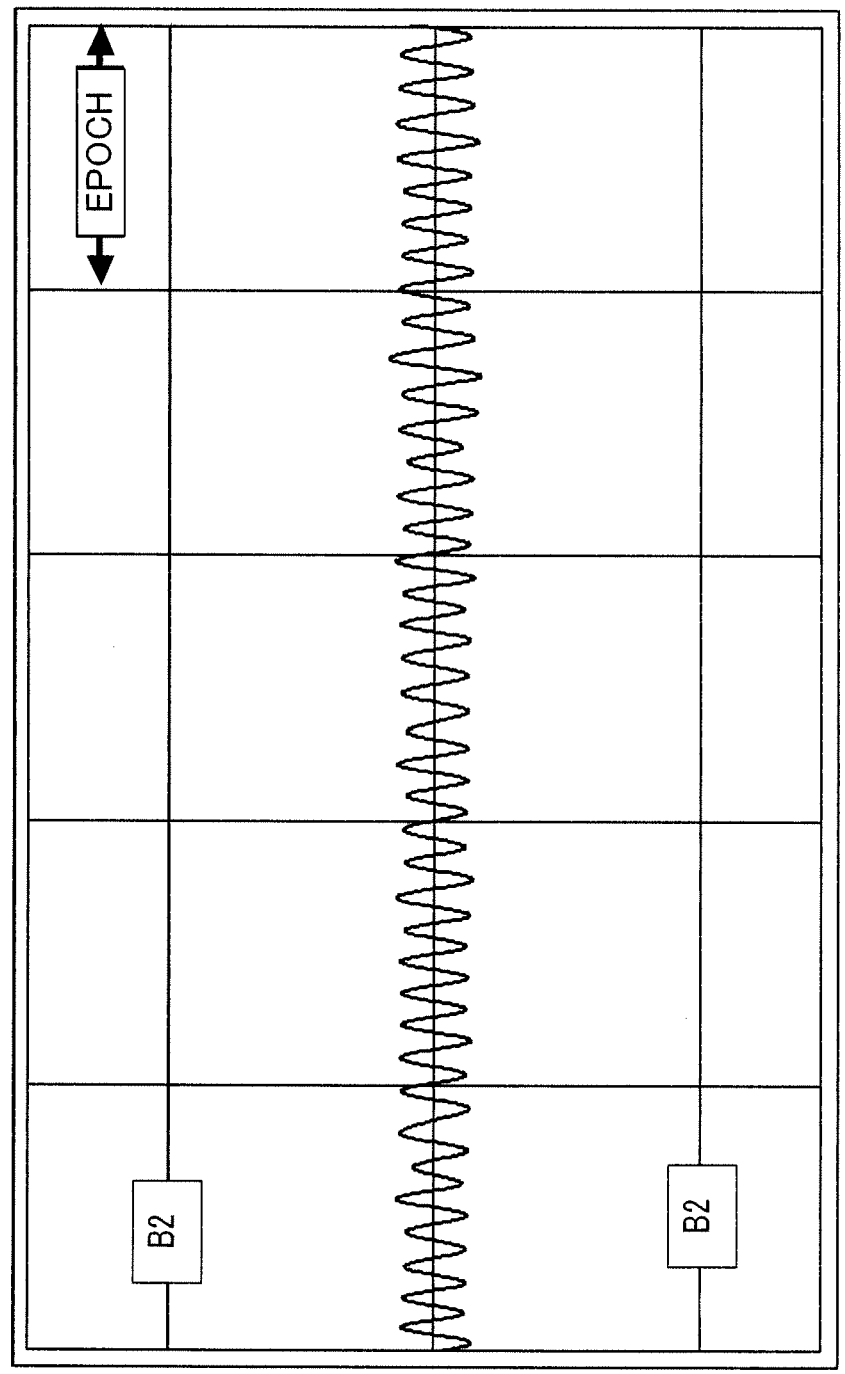
FIG. 8 is a diagram showing respiration waveforms in a state without movement (nonmovement state)
Figure 9:
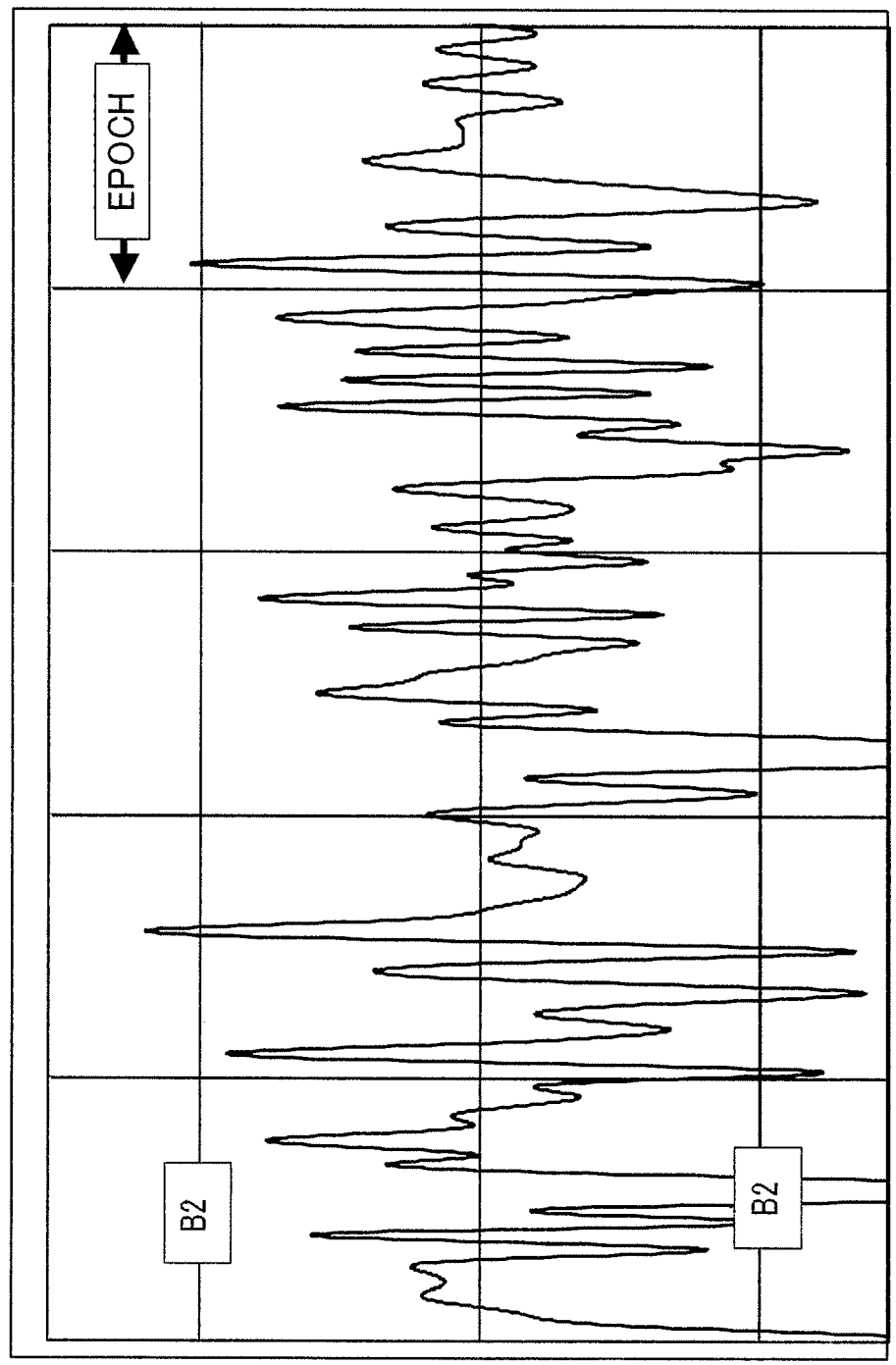
FIG. 9 is a diagram showing respiration waveforms in a state in which movement is large (large or gross movement state)
Figure 10:
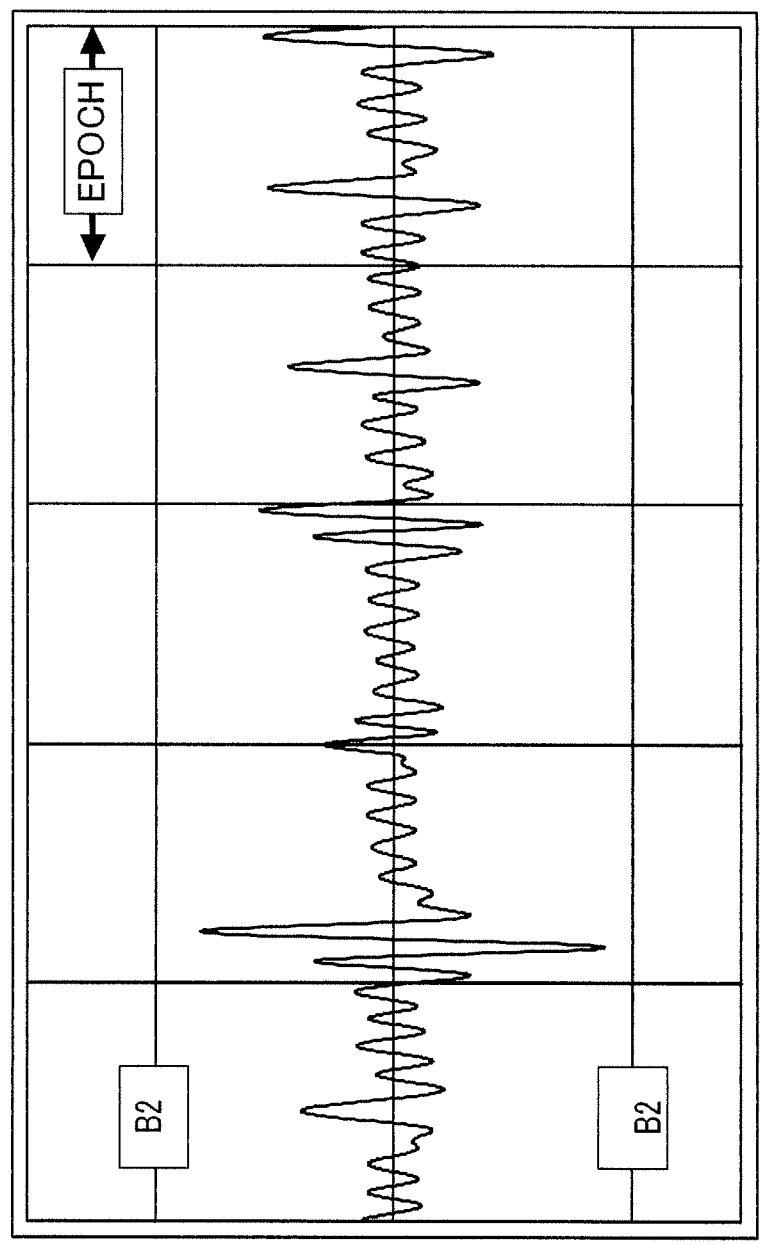
FIG. 10 is a diagram showing respiration waveforms in a state in which movement is slight (slight movement state)
Figure 11:
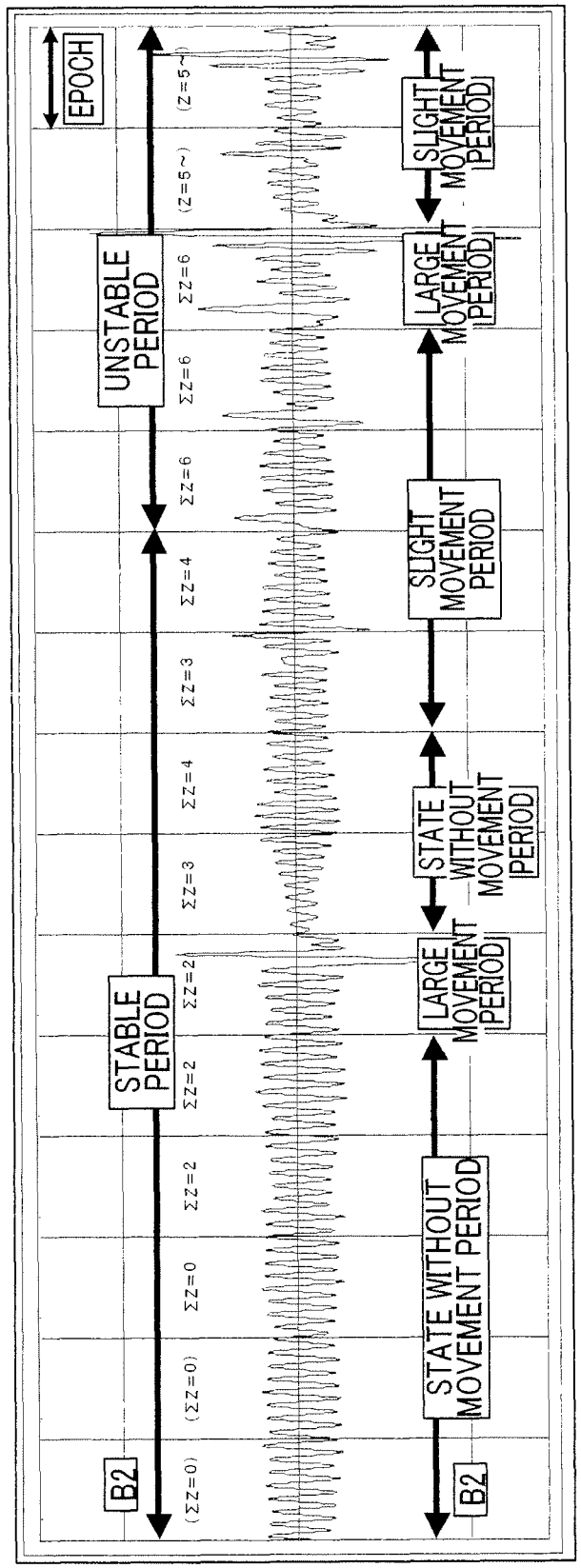
FIG. 11 is a diagram showing relationships between the body movement determination and an arousal determination.

FIG. 7 is next referred to, to describe the process performed by body movement determiner 12.

The process performed by body movement determiner 12 determines the magnitude of a body movement based on the amplitude of waveforms of respiratory signals for each waveform and then determines a body movement state in each epoch n as to whether there is any body movement that exceeds a certain threshold in the epoch n.

In Step S31, i is initially set as 0 (i=0), where i is the number of respirations and the total number of respirations from the start until the end of the measurement is imax times. Next in Step S32, i is incremented by 1, i.e., i=i+1, and the respiratory waveforms corresponding to respirations from i=1 (1-th) from the memory storage device 9.

Furthermore, in Step S32, body movement determiner 12 reads the respiratory waveforms corresponding to the i=i+2-th and i=i+3-th respirations and determines, based on the changes in the amplitudes of the consecutive three respiratory waveforms, whether there is any body movement. That is, it is determined whether the standard deviation of the amplitudes of the three respiratory waveforms is equal to or greater than B1, where B1 is a constant designating a threshold as to whether the respiratory waveforms are stable (Step S33). In a case in which the standard deviation is less than B1 (Step S33 is NO), it is determined that the respiratory waveforms are stable because the change in the respiration is small. Then, in Step S38, the subject respiration waveform (the i=i+1-th respiration waveform), from among the consecutive 3 respiratory waveforms, is assigned a state in which there is no movement (a state without movement or a nonmovement state) (see FIG. 8).

In a case in which the standard deviation is equal to or greater than B1, it is determined that there was a movement of the body because the fluctuation in respiration was large (Step S33 is YES). In Step S34, it is then determined whether the magnitude of the amplitude of the subject (i=i+1-th) respiration is equal to or greater than B2, where B2 is the maximum value of the amplitude of the respiratory waveform when the subject being examined is in the face-up position and B2 is a constant satisfying B2>A. In a case in which the magnitude of the amplitude of the concerned respiration waveform is equal to or greater than B2 (Step S34 is YES), the i=i+1-th respiration is assigned a large movement state in Step S35 (see FIG. 9). In a case in which the magnitude of the amplitude of the subject respiration waveform is less than B2 (Step S34 is NO), the routine proceeds to Step S36 in which the type of the body movement is determined based on the cycle of the respiratory waveform. Specifically, it is determined whether the respiratory cycle of the subject respiration waveform (i.e., either an interval between the subject respiration and the immediately previous respiration or an interval between the subject respiration and the immediately subsequent respiration) is equal to or greater than B3, where B3 is the maximum value of the cycle of the respiratory waveform when the subject being examined is in the face-up position. In a case in which this is affirmative (Step S36 is YES), the i=i+1-th respiration is assigned to a large movement state (Step S35). In a case in which the determination of Step S36 changes to NO, the subject respiration is assigned a slight movement state in Step S37 because the amplitude of and the cycle of the respiratory waveform are both small, but the fluctuation is large (see FIG. 10).

After each respiration is assigned to one of a large movement state, a slight movement state, or a state without movement, the determined state is stored in association with the corresponding respiration number i-th in memory storage device 9 in Step S39. In Step S40, it is then determined whether the body movement determination has been made for all the respirations imax, that is, whether i=imax is true. If the determinations for all the respirations are not finished (Step S40 is NO), the routine returns to Step S32 to repeat the body movement determination until the determinations on all the respirations are finished. If the determinations on all the respirations are finished (Step S40 is YES), the routine proceeds to Step S41 and the subsequent steps, in which the body movement is determined for each epoch n (see FIG. 11).

That is, in the same way as was performed in Steps S21 and S22 of FIG. 5, the epoch n is initially set as 0, i.e., n=0, in Step S41. In Step S42, the epoch n is incremented by 1, i.e., n=n+1, to read the respiratory data of the subject epoch and data of body movement states (a large movement state, a slight movement state, or a state without movement) that were assigned to respirations included in the subject epoch n and were stored in memory storage device 9 in Step S39. Then, in Step S43, it is determined whether there is any respiration that has been assigned a large movement state in the epoch n. If there is such a respiration in the epoch n, the determination changes to YES, and in Step S44, the epoch n is assigned a large movement period. If there is no such a respiration in the epoch n, the determination changes to NO, and it is further determined in Step S45 whether there is any respiration for which it is determined that there was a slight movement state in the epoch n. If there is a waveform that has been assigned a slight movement state in the epoch n, the determination changes to YES, and in Step S46, the epoch n is assigned a slight movement period. In a case in which the determination of Step S45 changes to NO, the epoch n is assigned a state without movement period (Step S47).

Once a large movement period, a slight movement period, or a state without movement period is thus assigned for the epoch n, the result of the determination is stored in association with epoch n in memory storage device 9 in Step S48. In Step S49, it is determined whether the body movement determination is performed for all the epochs nmax, and if this is not the case (i.e., n≠nmax), the determination changes to NO and the routine returns to Step S42 to repeat the body movement determination for the following epoch. Once the movement determination for all the epochs is finished (i.e., n=nmax) (Step S49 is YES), the routine then returns to the flowchart of FIG. 4 to advance to the next determination.

Figure 12:
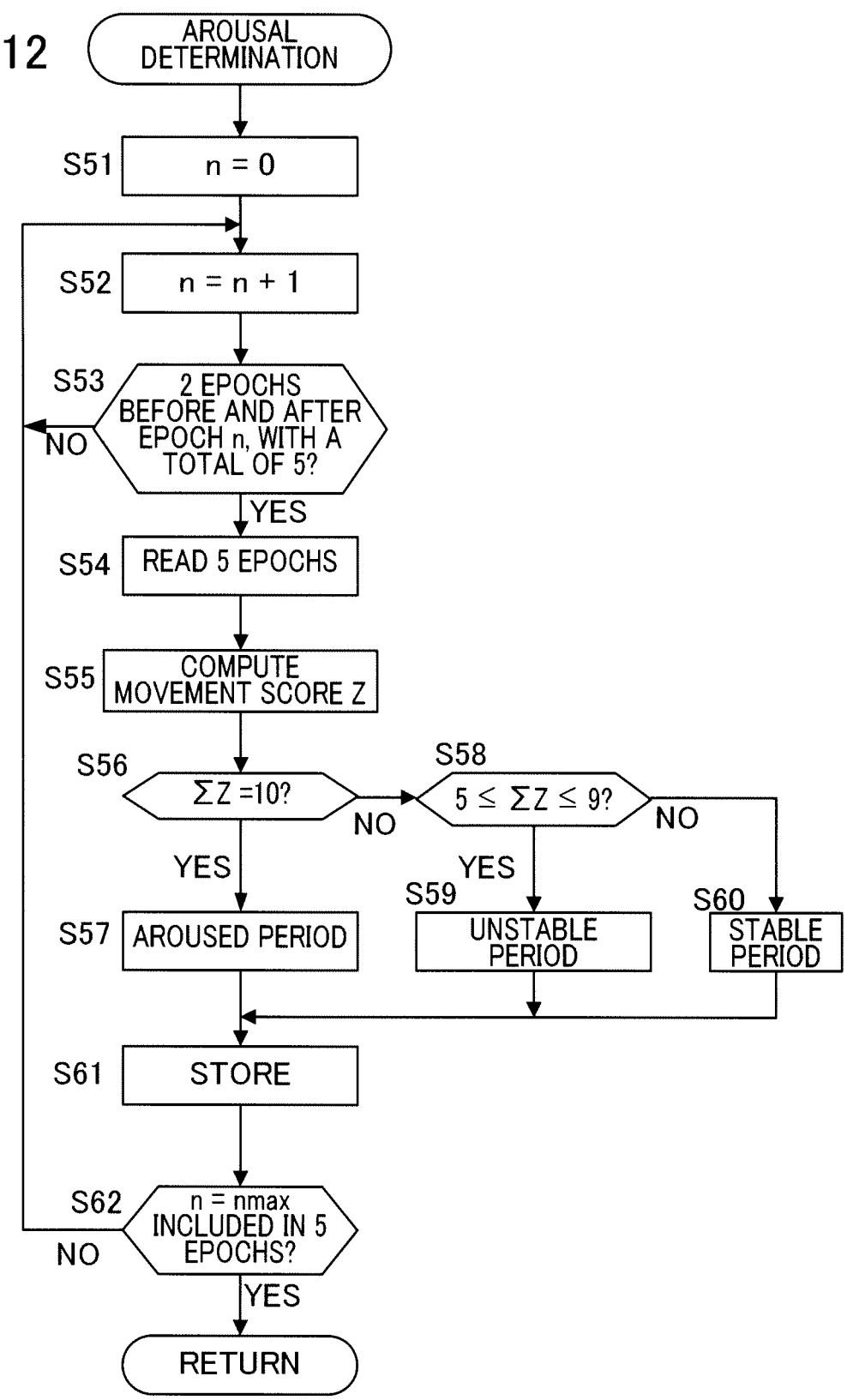
FIG. 12 is a flowchart showing a flow of the arousal determination process.

The flowchart of FIG. 12 is next referred to, in order to describe the process performed by arousal determiner 13.

In this determination process, the determination is performed for every epoch. Therefore, in Step S51, the epoch n is initially set to 0. In Step S52, the epoch n is incremented by 1, i.e., n=n+1, and then arousal determiner 13 reads data stored in association with the subject epoch n. In Step S53, it is determined whether there is stored, in memory storage device 9, the total of five epochs including the subject epoch n and two epochs each before and after. In a case in which there are no such five consecutive epochs, the routine returns to Step S52 and proceeds with n=n+1. In a case in which there are such five epochs, arousal determiner 13 reads data of body movements stored in association with the five epochs from the memory storage unit 9. In Step S55, a movement score Z is obtained for each of the five epochs. The movement score Z is a value defined as Z=2 for a large movement period, Z=1 for a slight movement period, and Z=0 for a state without movement period. The movement score for each of the five epochs are obtained based on the results of the body movement determination performed by body movement determiner 12 described in details with reference to FIG. 7. Furthermore, the total of the movement scores Z of the five epochs is obtained based on the movement score Z for each of the five epochs, where 0≤the total Z≤10. The total Z will be hereinafter referred to as "ΣZ" (refer to FIG. 11).

In Step S56, it is determined whether the total of movement scores ΣZ for the five epochs is equal to 10, i.e., whether all of the five epochs are large movement periods. In a case in which the determination changes to YES, the epoch n read in Step S52, i.e., an epoch in the middle of the 5 epochs, is assigned an aroused period in Step S57. In a case in which the total of the movement scores ΣZ is less than 10, the determination changes to NO. In Step S58, it is then determined whether 5≤ΣZ≤9 is true. In a case in which the determination changes to YES, that the epoch n is assigned an unstable period that is highly likely a REM sleep or a light sleep state in which respiratory states are relatively unstable (Step S59). In a case in which ΣZ does not lie within the range, i.e., ΣZ≤4 is true, the determination of Step S58 changes to NO. Therefore, in Step S60, the epoch n is assigned a stable period that is highly likely a deep sleep or a light sleep state in which respiratory states are relatively stable.

Once the determination is thus made to assign one of an aroused period, an unstable period, or a stable period, to the subject epoch n, the result of the determination is stored in association with the epoch n in memory storage device 9 in Step S61. In Step S62, it is determined whether the epoch nmax is included in the five epochs. In a case in which the determination changes to NO, the routine returns to Step S52 to again start the arousal determination for the next epoch by setting n=n+1. If there is the epoch nmax in the five epochs, the determination of Step S62 changes to YES, and the routine returns to the flowchart of FIG. 4 and proceeds to the next determination.

Figure 13A:
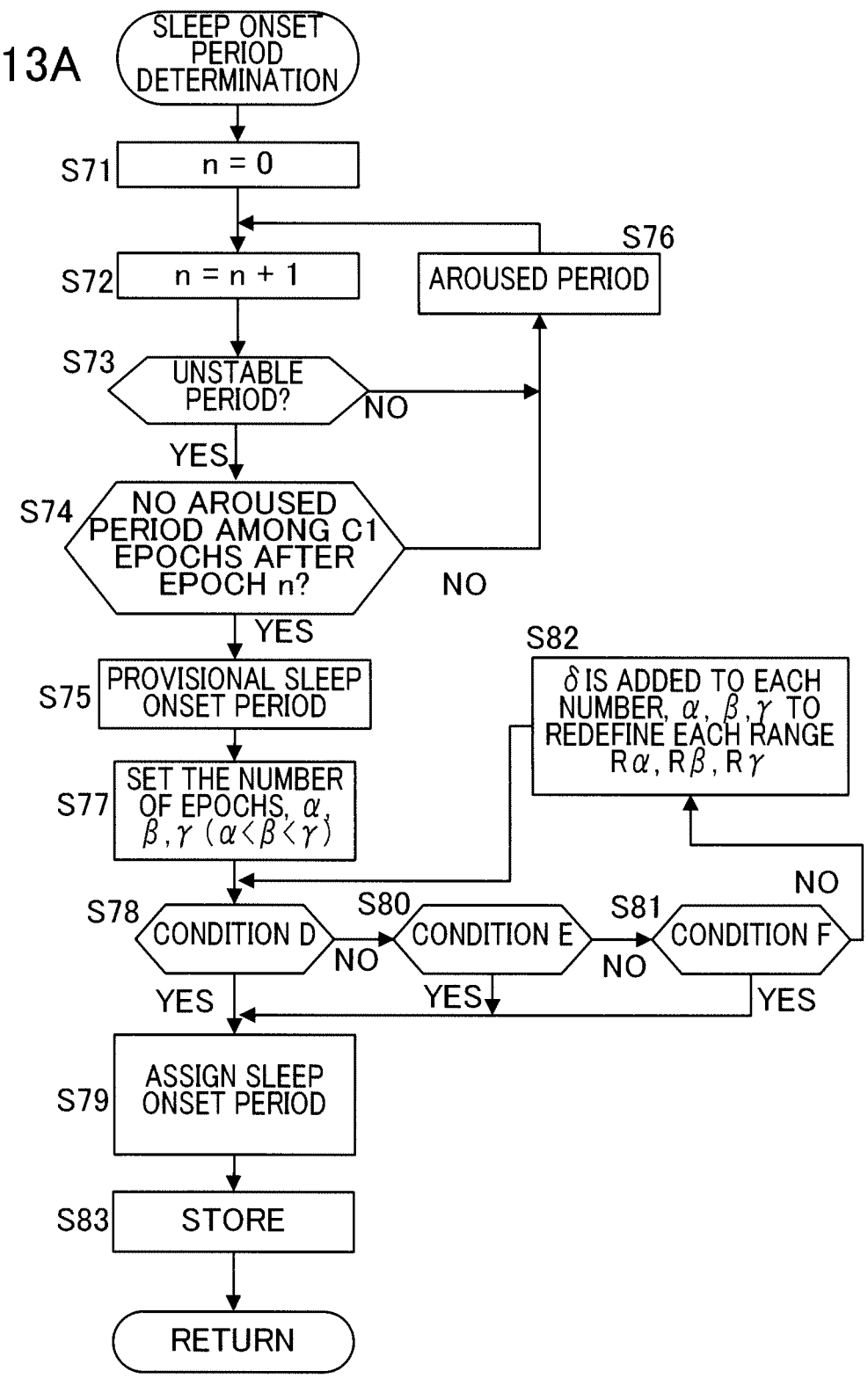
FIG. 13A is a flowchart showing a flow of a sleep onset period determination process.
Figure 13B:
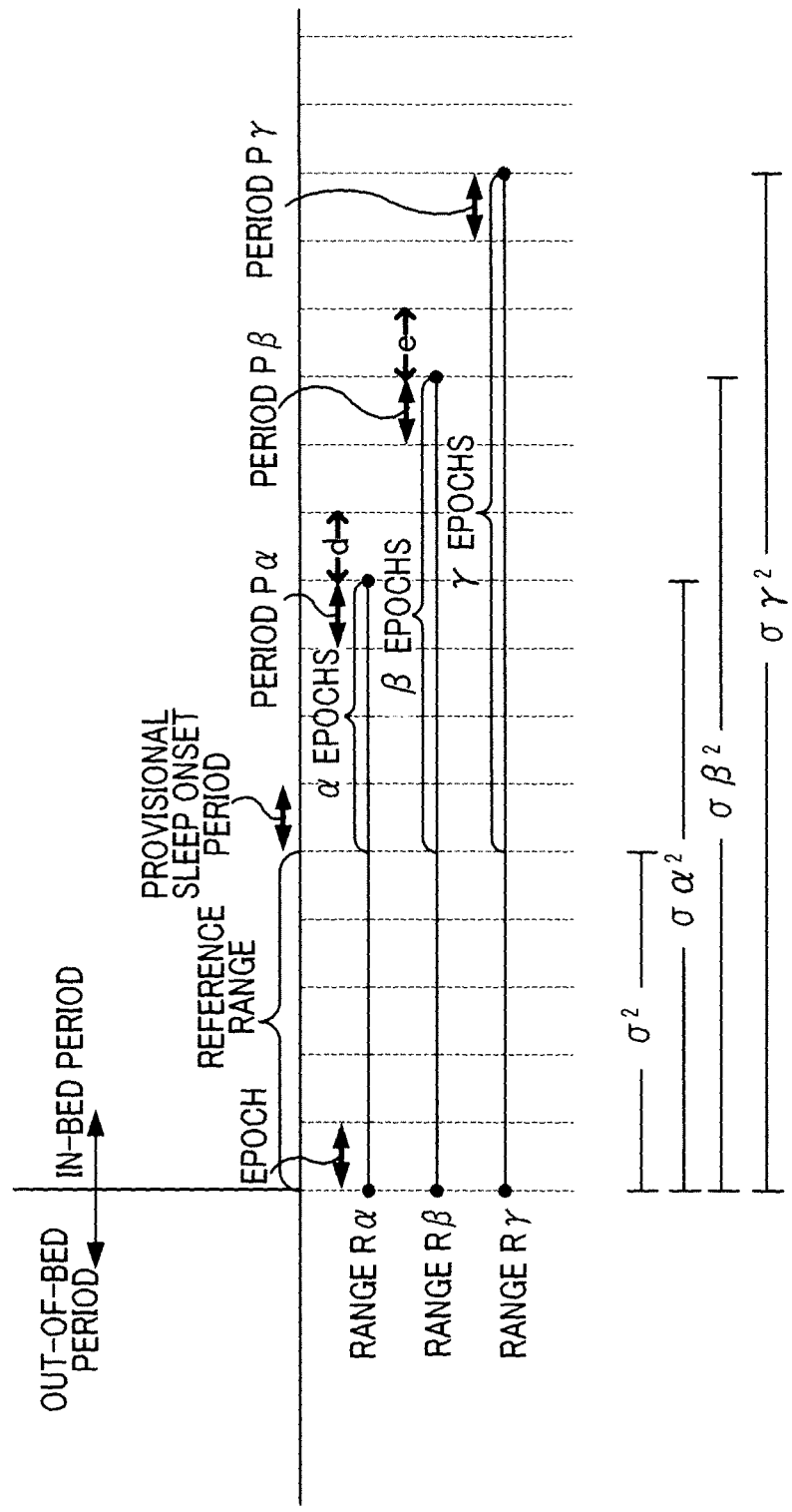
FIG. 13B is a diagram for describing the details of conditions used in the sleep onset period determination process.

FIGS. 13A and 13B are next referred to, to describe the process performed by sleep-onset period determiner 14.

Sleep-onset period determiner 14 determines an epoch in which the subject being examined transitions from an initial aroused state (full wakefulness) right after lying down to having fallen asleep (hereinafter referred to as a "sleep-onset period"). In this determination, the sleep-onset period is determined by identifying an initial aroused state more specifically based on tendencies in falling asleep, in addition to the aroused period determination that has been performed based on the movement score Z by arousal determiner 13, which has been described previously with reference to FIG. 12.

In this determination process, the determination is performed for every epoch as was performed in the previous determinations. Therefore, in Step S71 of FIG. 13A, the epoch n is initially set to 0. In Step S72, the epoch n is incremented by 1 (n=n+1), and sleep-onset period determiner 14 then reads data indicating an aroused period, an unstable period, or a stable period assigned to the subject epoch n in the arousal determination process. In Step S73, it is determined whether the read epoch n is an unstable period, in which, however, this unstable period is one that appears for the first time after the initial aroused periods. In a case in which the epoch n is not an unstable period, the determination of Step S73 changes to NO. In Step S76, the epoch n is regarded as an aroused period and overwrites what is stored in association with the subject epoch n in memory storage device 9 accordingly. The routine then repeats the processes of Step S72 and the subsequent steps until it hits an epoch that is an unstable period. Even in a case in which the subject epoch n has been assigned a stable period that is highly likely a deep sleep state or a light sleep state, this epoch is regarded as an aroused period in the present embodiment because, in normal breathing activity of humans, it is unlikely that a stable state will appear immediately after lying down without passing through an unstable state, and hence it can be readily inferred that data showing the stable period is not reliable.

In a case in which the epoch n is an unstable period, the determination of Step S73 changes to YES, and it is then determined in Step S74 whether there is any epoch that has been assigned an aroused period among as many as C1 epochs starting from the epoch n. The C1 epochs correspond to a range in which a person does not normally arise immediately after falling asleep in a case in which the epoch n is a sleep-onset period because it is unlikely for humans to arise immediately after falling asleep. Therefore, in a case in which there is any aroused state during C1 epochs starting from the epoch n, the determination changes to NO, and the epoch n is regarded as an aroused period. In Step S76, what is stored in memory storage device 9 is overwritten accordingly, and the routine then repeats the process of Step S72 and the subsequent steps. In a case in which the determination of Step S74 changes to YES, the epoch n is regarded as a provisional sleep-onset period in Step S75. The routine then proceeds to the processes of Step S77 and the subsequent steps, to more specifically identify a sleep-onset period.

In the processes starting from Step S77, it is determined up to which epoch is to be regarded as aroused periods and is to be redefined as aroused periods, from among epochs that have been determined as unstable periods on and after the provisional sleep-onset period, and an epoch immediately following the most recent aroused period is assigned a sleep-onset period. The determination is performed based on three types of respiratory variation patterns around the sleep-onset period of a human, the patterns having been found by the inventor through actual measurements.

As shown in FIGS. 13A and 13B, in Step S77, a range starting from the first epoch determined as an in-bed period to an epoch immediately previous to the provisional sleep-onset period is set as a reference range, from among epochs that have been determined as in-bed periods by in-bed or out-of-bed determiner 11 described in detail by using FIG. 5. The respiratory data corresponding to the epochs included in the reference range are read from memory storage device 9, and the variance $\sigma^2$ of respiratory rates for each epoch in the reference range is obtained. Furthermore, a range including the reference range and also including a certain number $\alpha$, $\beta$, or $\gamma$ of additional epochs starting from the provisional sleep-onset period is defined respectively as Range R$\alpha$, Range R$\beta$, and Range R$\gamma$, and each epoch delimiting each range is called Period P$\alpha$, Period P$\beta$, or Period P$\gamma$, respectively. The $\alpha$, $\beta$, and $\gamma$ are constants satisfying the relationship $\alpha<\beta<\gamma$ and are set by finding a period suited for discriminating among the three types of respiratory variation patterns based on actual measurements. The respiratory data corresponding to the epochs included in each of Range R$\alpha$, Range R$\beta$, and Range R$\gamma$ are read from memory storage device 9, and the variances $\sigma\alpha^2$, $\sigma\beta^2$, and $\sigma\gamma^2$ of respiratory rates in each of these ranges are obtained in the same way as it was done for the reference range. The three types of respiratory variation patterns respectively as Conditions D, E, and F are tested using the variances $\sigma^2$, $\sigma\alpha^2$, $\sigma\beta^2$, and $\sigma\gamma^2$.

In the first respiratory variation pattern, the fluctuation in respiratory rate of the subject being examined is rapidly reduced, and the subject being examined then transitions to a sleep state. Therefore, in Step S78, the first respiratory variation pattern is tested by Condition D being "$\sigma\alpha^2>\sigma\beta^2$ (Equation A)" and "$\sigma\beta^2 \le C2$ (Equation B)". That is, as indicated by Equation A, the fluctuation in the respiration rate is reduced as the range is widened. As indicated by Equation B, the variance for the increased population is smaller than a certain value C2, where C2 is a constant that can be used for determining a value of variance to be significantly close to the fluctuation in respiratory rate, the fluctuation appearing after falling asleep. It is determined that the subject being examined is in a sleep state already in Period P$\beta$ if Condition D is satisfied, and the determination of Step S78 changes to YES.

In Step S79, it is determined that a period at least up to Period P$\alpha$ is an aroused period, and an epoch "d" right after Period P$\alpha$ is defined as a sleep-onset period. In a case in which Condition D is not satisfied (Step S78 is NO), the routine then proceeds to Step S80 to perform determination on the second respiratory variation pattern based on Condition E.

In the second respiratory variation pattern, the fluctuation in respiratory rate of the subject being examined is gradually reduced, and the subject being examined then transitions to a sleep state. Therefore, this pattern is determined based on Condition E defined by an equation "$\sigma^2 * C3 \ge \sigma\alpha^2 \ge \sigma\beta^2$ (Equation C)", where C3 is a constant satisfying C3<1 and is for reducing the fluctuation in respiratory rate in the reference range by a certain percentage. C3 also satisfies $\sigma^2 * C3 > C2$, C2 being a constant used in Equation B. Accordingly, as indicated by Equation C, the fluctuation in respiratory rate in Range R$\alpha$ is equal to or smaller than the fluctuation in the reference range reduced by C3, and the fluctuation in Range R$\beta$ is equal to or less than that in Range R$\alpha$.

In a case in which Condition E is satisfied (Step S80 is YES), it is determined in Step S79 that additional periods up to Period P$\beta$ are aroused periods because the degree of fluctuation is decreasing, although gradually. Therefore, an epoch "e" immediately after Period P$\beta$ is assigned to a sleep-onset period. In a case in which Condition E is not satisfied (Step S80 is NO), the routine proceeds to Step S81 to perform determination on the third respiratory variation pattern.

In the third respiratory variation pattern, the fluctuation in respiratory rate of the subject being examined once becomes larger than that in the reference range and then becomes smaller. Therefore, this pattern is determined based on Condition F defined by equation "$\sigma^2<\sigma\beta^2$ (Equation D)" and "$\sigma\gamma^2<\sigma\beta^2$ (Equation E)". Range R$\beta$ and Range R$\gamma$ are used in Condition F because this third pattern is observed over a relatively longer span of time in comparison with the first and the second patterns.

In a case in which Condition F is satisfied (Step S81 is YES), it is determined in Step S79 that at least until the end of Period P$\beta$ of Range R$\gamma$ is an aroused period because the degree of the fluctuation increases in Period Pβ. Therefore, an epoch "e" immediately after Period Pβ is assigned a sleep-onset period.

In a case in which Condition F is not satisfied (Step S81 is NO), i.e., none of Conditions D, E, and F are satisfied, the routine proceeds to Step S82, in which the number of epochs in each Range Rα, Range Rβ, and Range Rγ is increased by the 6 number of epochs, to redefine Range Rα, Range Rβ, and Range Rγ. The routine then returns to Steps S78, and the determinations based on Conditions D, E, and F are repeated until a sleep-onset period is finally determined.

Once the sleep onset period is determined in Step S79, in Step S83, a sleep-onset period is stored in association with the epoch that was assigned a sleep onset period in Step 79. Furthermore, the epochs from the epoch assigned as the provisional sleep onset period in Step S75 to an epoch immediately previous to the sleep onset period are stored as aroused periods. The routine then returns to the flowchart of FIG. 4 to proceed to the next determination.

Figure 14:
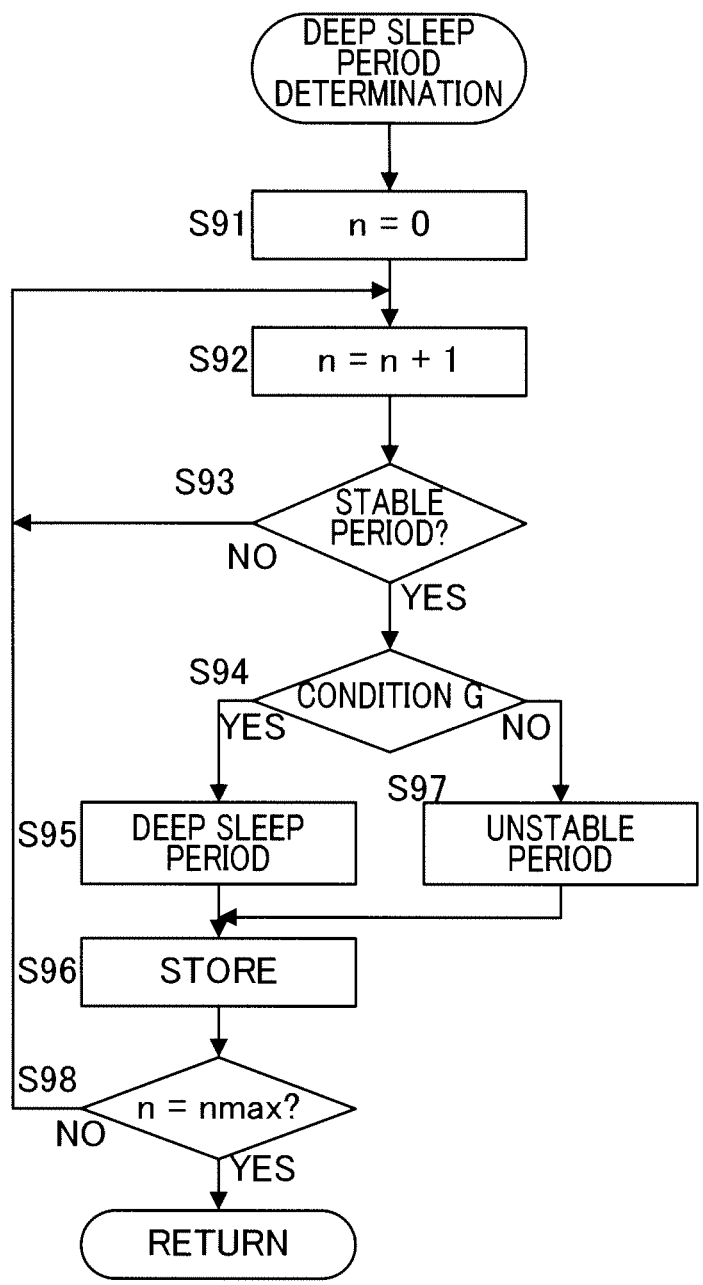
FIG. 14 is a flowchart showing a flow of a deep sleep period determination process.

Description will next be given of a process performed by deep sleep period determiner 15 with reference to the flowchart of FIG. 14.

When respiration is moderate and is in a uniform rhythm in the deep sleep state, and therefore there should be little body movement, based on this, a determination is performed as follows.

The deep sleep period determination process is performed for each epoch as described above. Therefore, in Step S91, the epoch n is initially set as 0. In Step S92, the epoch n is incremented by 1 (n=n+1), and arousal determination result data indicating an aroused period, a stable period, or an unstable period for the subject epoch n are read from memory storage device 9, the arousal determination having been performed in the arousal determination process described in details in FIG. 12. In Step S93, it is determined whether the read epoch n is a stable period. In a case in which the epoch n is not a stable period (Step S93 is NO), the routine returns to Step S92 to proceed to the next epoch by incrementing n by 1 (n=n+1), and the determination of Step S93 is repeated until it reaches an epoch that is a stable period. In a case in which the epoch n is a stable period (Step S93 is YES), a determination based on Condition G is performed in Step S94, Condition G including several conditions.

The epoch n is determined as a deep sleep period in a case in which all of the following conditions defined in Condition G are satisfied: "the respiratory rate in the subject epoch n≤H1"; and "the standard deviation of cycles of respirations in the epoch n≤H2"; and "the difference in the respiratory rate between the epoch n and an epoch immediately before the epoch n≤H3"; and "the difference in the respiratory rate between the epoch n and an epoch immediately after the epoch n≤H3"; and "the epoch n is a non movement period", where H1, H2, and H3 are constants obtained based on actually measured values.

In Step S94, in a case in which the subject epoch n satisfies Condition Q the epoch n is assigned a deep sleep period in Step S95, and, in Step S96, the result of the determination is stored in memory storage device 9. In a case in which the subject epoch n does not satisfy Condition G (Step S94 is NO), the subject epoch n is assigned an unstable period in Step S97, and in Step S96, data showing the unstable period is stored in memory storage device 9 in association with the epoch n in place of data showing the stable period. In Step S98, it is determined whether the deep sleep period determination is made for all the epochs nmax. In a case in which the deep sleep period determination is not performed for all the epochs (Step S98 is NO), the routine returns to Step S92 to repeat the process at that point and thereafter. In a case in which the deep sleep period determination is performed for all the epochs (Step S98 is YES), the routine returns to the flowchart of FIG. 4 and proceeds to the next determination.

Figure 15:
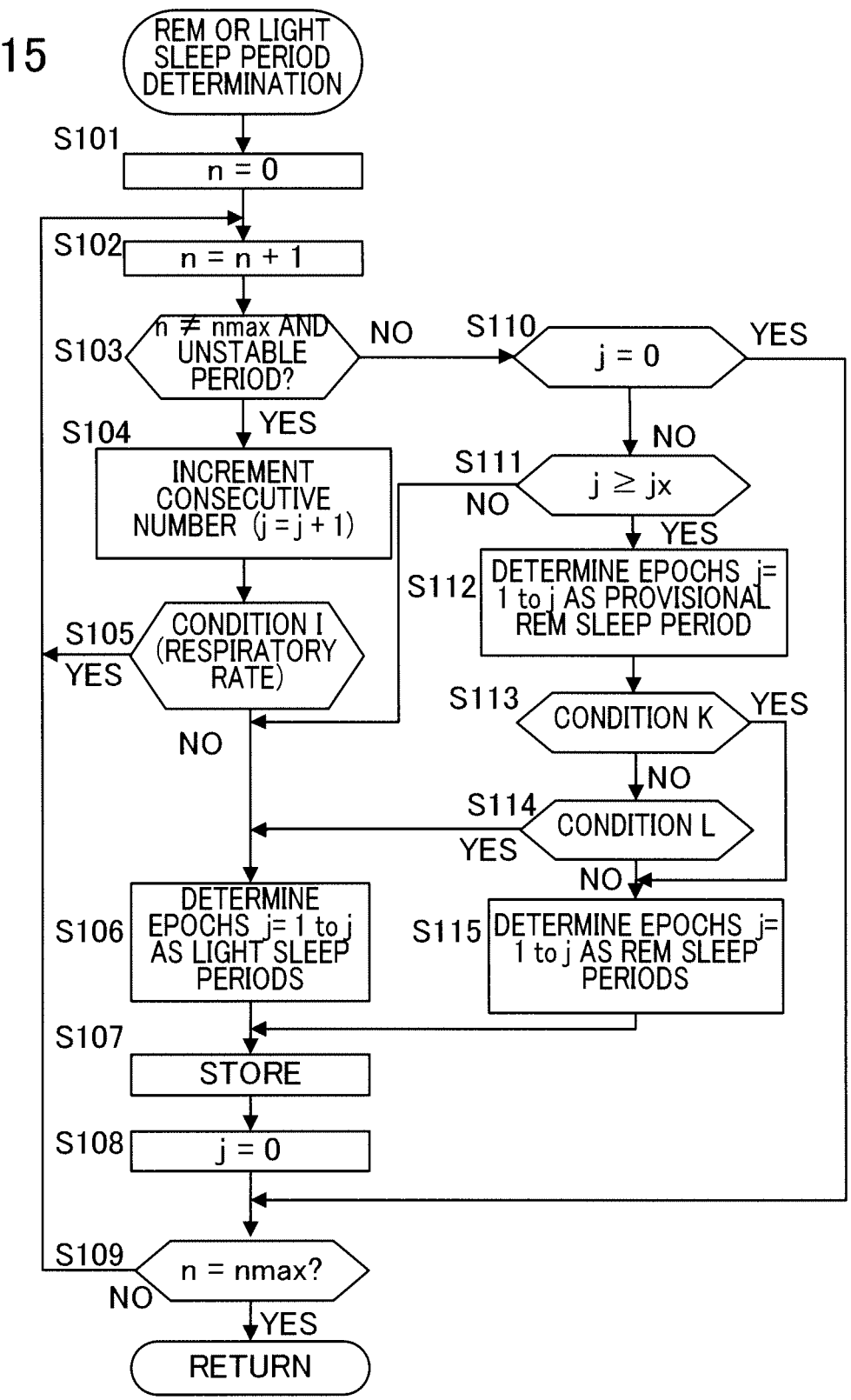
FIG. 15 is a flowchart showing a flow of a REM or light sleep period determination process.

Description will next be given of a process performed by REM or light sleep period determiner 16, with reference to the flowchart of FIG. 15.

The REM or light sleep period determination is performed for each epoch. Therefore, in Step S101, the epoch n is initially set as 0. In Step S102, the epoch n is incremented by 1 (n=n+1), and respiratory data corresponding to the subject epoch n and data indicating an aroused period, a stable period, or an unstable period for the subject epoch n are read from memory storage device 9.

In Step S103, it is determined whether the read epoch n is not nmax (n≠nmax) and is an unstable period described with reference to FIG. 12. In a case in which epoch n≠nmax is satisfied and in which the epoch n is an unstable period (Step S103 is YES), the routine proceeds to Step S104, in which j indicating the number of consecutive epochs that are unstable period is incremented by 1 (j=j+1), where the initial value of j is 0. In the following Step S105, the determination based on Condition I is performed, Condition I being "the average of the respiratory rates of epochs over all the in-bed periods≤the respiratory rate in the epoch n". That is, as described above, because the respiratory rate increases in the REM sleep, it is determined whether the respiratory rate in the epoch n is larger than the average respiratory rate during sleep.

In a case in which Condition I is not satisfied (Step S105 is NO), each epoch from j=1 to j is assigned a light sleep period in Step S106. In a case in which Condition I is satisfied (Step S105 is YES), the routine returns to Step S102 in which the epoch n is incremented by 1 and repeats the following steps.

In a case in which the epoch n is nmax (n=nmax) and is not an unstable period (Step S103 is NO), it is determined in Step S110 whether the number of consecutive epochs, j, that are unstable period is 0, i.e., j=0. The determination changes to NO if the number of consecutive epochs is 0, and the routine proceeds to Step S111, in which it is determined whether j is equal to or larger than a certain number jx (j≥jx), the determination being performed for an unstable period that satisfies Condition I and that has the consecutive numbers from j=1 to j, where jx is the number of consecutive epochs that is set so that, when the unstable periods stays for the jx number of times, the epoch n is possibly a REM sleep state. In a case in which the consecutive number j does not exceed jx (Step S111 is NO), the epochs from j=1 to j are determined as light sleep periods in Step S106. In a case in which the consecutive number j exceeds jx or is equal to jx (Step S111 is YES), the epochs from j=1 to j are regarded as being highly likely to be REM sleep states and are determined to be provisional REM sleep periods in Step S112.

In a case in which there is any state in which no respiration is detected, such as may occur due to sleep apnea, labored respiration takes place. Therefore, the respiratory rate in the epoch n in Condition I used in the determination of Step S105 increases, and the determination of Step S105 is performed based on an abnormal value. As a result, an epoch that is to be determined as a light sleep period can be mistakenly determined to be a REM sleep period. To prevent such an erroneous determination, the determination of Step S 113 is performed, in which determination Condition K being "the number of stable periods in all the in-bed periods/(the number of all the in-bed periods−the number of aroused periods)≥k" is tested to determine whether stable periods (i.e., a deep sleep state or light sleep state) during sleep are observed more than a predetermined percentage k, so as to determine whether sleep that is at least generally regarded as normal is maintained. In a case in which Condition K is satisfied, it is determined that the sleep is normal and that the result of the determination based on Condition I is valid. In a case in which the determination of Step S113 changes to YES, the epochs starting from j=1 to j are determined to be REM sleep periods in Step S115. In a case in which Condition K is not satisfied, it is determined that there was an abnormal sleep state (Step S113 is NO), and an additional determination based on the following Condition L is performed in Step S114.

Condition L is tested by determining, during the provisional REM sleep periods from j=1 to j, "(the maximum respiratory rate–the minimum respiratory rate)/the number of provisional REM sleep periods≥Lx" to determine whether the fluctuation in the respiratory rate is in a normal range, where Lx indicates that, if a value is equal to or larger than Lx, respiration is abnormal, meaning that a state in which no respiration is detected appears in at least one of the provisional REM sleep periods from j=1 to j. Therefore, in a case in which Condition L is satisfied, i.e., respiration is abnormal, the determination changes to YES, and in Step S106, the provisional REM sleep periods from j=1 to j are determined to be light sleep periods. In a case in which Condition L is not satisfied, i.e., respiration is normal, the determination changes to NO, and in Step S115, the provisional REM sleep periods from j=1 to j are determined to be REM sleep periods.

Once REM sleep periods and light sleep periods are determined, the results of the determinations are stored in association with each epoch n in memory storage device 9. In Step S108, the number of consecutive unstable periods j is initialized to 0. In Step S109, it is determined whether the REM sleep or light sleep determination has been performed for all the epochs nmax. In a case in which the determination has not been made for all the epochs (Step S109 is NO), the processes from Step S102 are repeated until the determinations for all the epochs are completed. In a case in which the determinations for all the epochs have been completed (Step S109 is YES), the routine returns to the flowchart of FIG. 4 to advance to the next determination.

Figure 16:
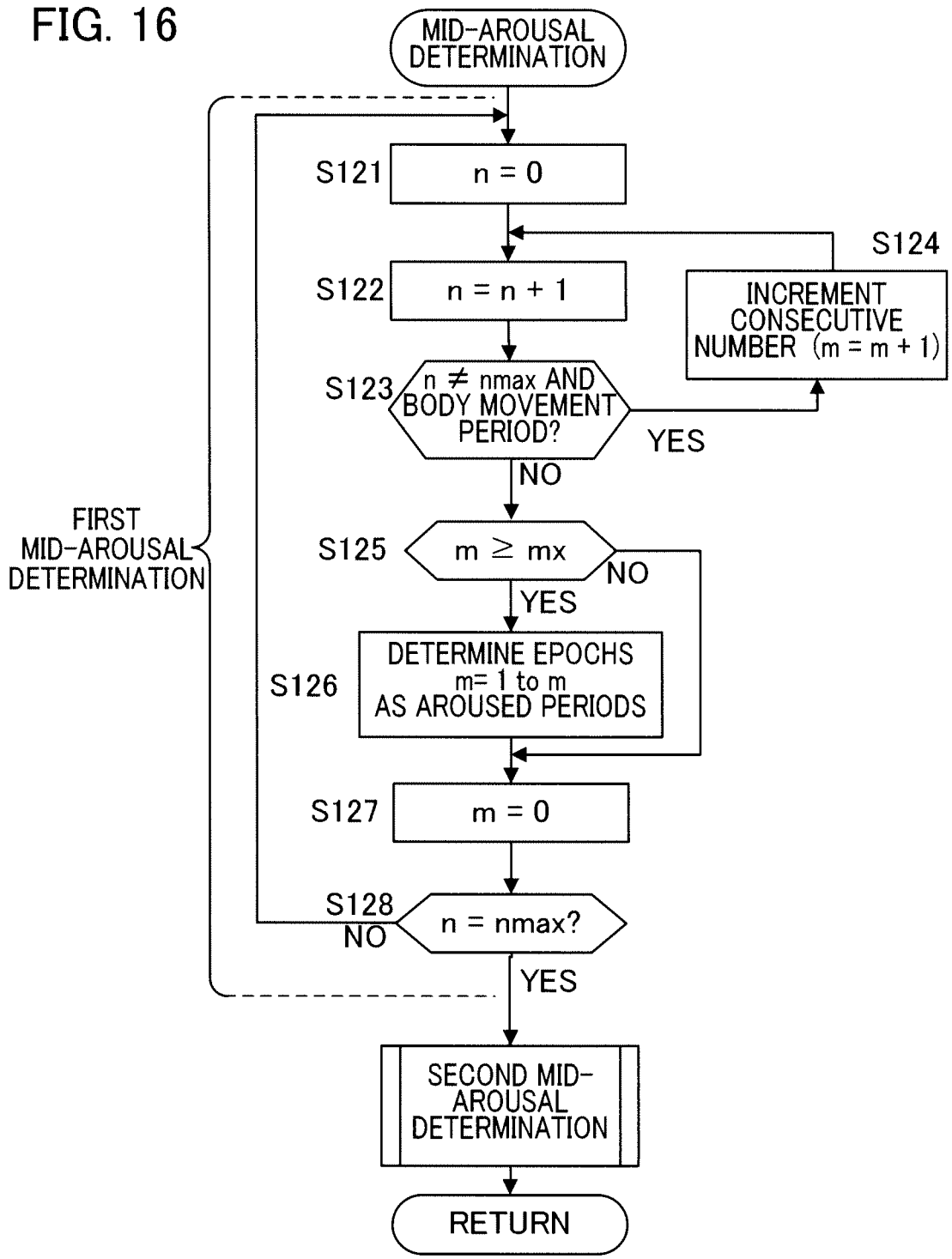
FIG. 16 is a flowchart showing a flow of a mid-arousal determination process.

Description will be next given of a process performed by mid-arousal determiner 17 with reference to the flowchart of FIG. 16.

The mid-arousal determination process is performed in the following way because a subject is considered as having been awakened in the midst of sleep in a case in which body movement persists for longer than a certain period of time even in the sleep state. The mid-arousal period determination process of the present embodiment has two stages: a first mid-arousal determination process and a second mid-arousal determination process.

In the first mid-arousal determination process, in Step S122, the epoch n is initially set as 0. In Step S102, the epoch n is incremented by 1 (n=n+1), and data indicating a large movement, a slight movement period, or a state without movement period for the subject epoch n is read from memory storage device 9. In Step S123, it is determined whether the read epoch n is not nmax (n≠nmax) and is either a large movement period or a slight movement period (hereinafter referred to as a "body movement period") from among a large movement period, a slight movement period, and a state without movement period that were determined by body movement determiner 12 described in detail in FIG. 7.

In a case in which the epoch n satisfies n≠nmax and is a body movement period, i.e., the epoch is not the final epoch nor is it a state without movement period, the determination changes to YES. In Step S124, the number of consecutive such epochs is counted as m=m+1, where the initial value of m is 0. The routine then proceeds to Step S122, in which the epoch n is incremented by 1 (n=n+1) to repeat the detection of a body movement period. In a case in which the epoch n is n=nmax or is not a body movement period, the determination changes to NO, and in Step S125, it is determined whether the consecutive number m is equal to or larger than mx (i.e., m≥mx), where mx is the number of consecutive body movement periods indicating possibility of mid-arousal. When m≥mx is satisfied (Step S125 is YES), it is determined in Step S126 that the epochs from m=1 to m are aroused states. These epochs are redefined as "aroused states" and are stored in memory storage device 9 accordingly even if each epoch is stored in association with a deep sleep period, a light sleep period, or a REM sleep period. Then, in Step S127, the consecutive number m is once initialized to zero.

In a case in which the consecutive number m does not exceed mx, the determination of Step S125 changes to NO, and then in Step S127, the consecutive number m is initialized to zero. In Step S128, it is determined whether the first mid-arousal determination is performed for all the epochs nmax, and the determination changes to NO in a case in which the determination for all the epochs is not finished. The routine then returns to Step S121 to repeat the first mid-arousal determination process. In a case in which the first mid-arousal determination is finished for all the epochs, the determination of S128 changes to YES, and then a mid-arousal state will be closely determined based on several conditions in the second mid-arousal determination process as will be described in FIG. 17. The conditions tested in the second mid-arousal determination process are derived from the actually measured values by the inventor and are defined based on mid-arousal patterns of humans. After the second mid-arousal determination process is performed, the routine in the flowchart of FIG. 4 returns and advances to the next determination.

Figure 17:
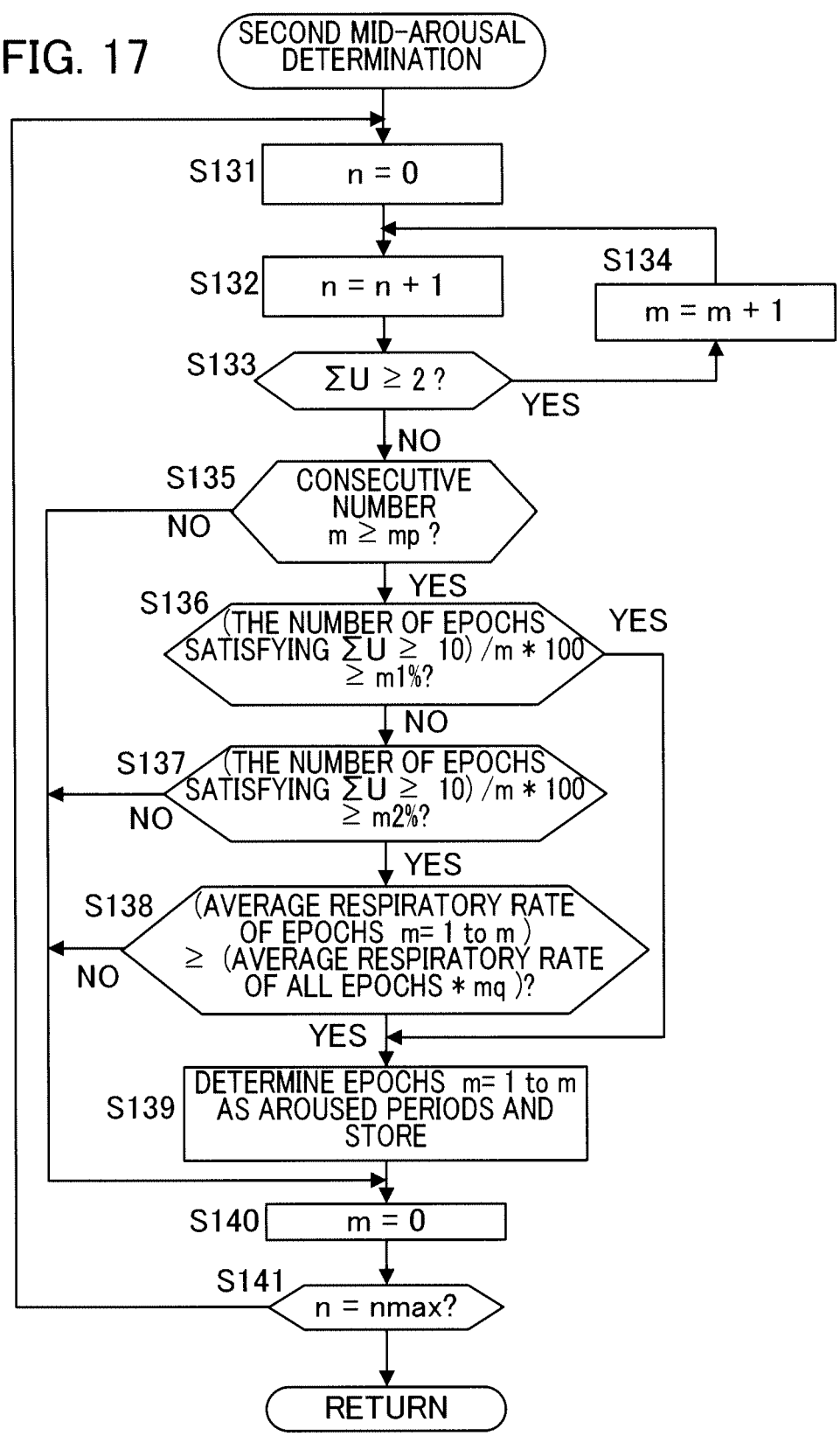
FIG. 17 is a flowchart showing a flow of a second mid-arousal determination process.

The flowchart of FIG. 17 is now referred to in order to describe the second mid-arousal determination. In this determination, in Step S131, the epoch n is initialized as 0, and in Step S132, the epoch n is incremented by 1 (n=n+1), to read data indicating a large movement state, a slight movement state, or a state without movement corresponding to each respiration i of the epoch n.

In Step S133, a state of body movement in each epoch n is first obtained. That is, a large movement state is set as U=2, a slight movement state is set as U=1, and a state without movement is set as U=3, for each state stored in association with 1 respiration i in Step S39 of the flowchart of FIG. 7 in the previous description on body movement determiner 12. The state of body movement of the subject epoch n is obtained by the sum of Us (hereinafter referred to as ΣU) during the epoch, each U corresponding to each respiration i.

It is then determined whether, in the epoch n, ΣU≥2 is satisfied. If ΣU≥2 is true, the determination changes to YES, and in Step S134, the consecutive number is counted as m=m+1, where m is initially set to 0. Furthermore, if it is not true that ΣU≥2, the determination changes to NO, and the routine advances to Step S135 without incrementing the consecutive number m. In Step S135, it is determined whether the current count number m is equal to or larger than mp (m≥mp), where mp is a constant showing the number of consecutive body movement periods indicating possibility of mid-arousal and satisfying mp<mx. In a case in which m≥mp is not satisfied, it is determined that there is no possibility of mid-arousal, and the determination of Step S135 changes to NO. Then in Step S140, the consecutive number m is initialized to 0. In a case in which m≥mp is true, it is inferred that the epochs n from the consecutive number m=1 to m=m are aroused states, and the determination of Step S135 changes to YES. The routine then proceeds to the next condition-based determination.

In Step S136, it is determined whether a condition "(the number of epochs n satisfying $\Sigma U \geq 10$)/m*100$\geq$m1%)" is satisfied for the epochs n from the consecutive number m=1 to m=m, where m1 is a constant showing a proportion to the latest consecutive number m. If the condition is satisfied, the determination changes to YES, and in Step 139, the epochs from the consecutive number m=1 to m are redefined as aroused states and are stored in memory storage unit 9. In a case in which the above condition is not satisfied, the determination changes to NO, and the routine proceeds to the next determination.

In Step S137, it is determined whether a condition "(the number of epochs n satisfying $\Sigma U \geq 10$)/m*100$\geq$m2%)" is satisfied for the epochs n from the consecutive number m=1 to m, where m2 is a constant that is in a proportion to the latest consecutive number m and satisfies m2<m1. If the condition is not satisfied, it is regarded that there is no possibility of mid-arousal during the epochs from m=1 to m=m, and the determination changes to NO. Then in Step S140, the consecutive number is initialized to 0 (m=0). In a case in which the above condition is satisfied, it is regarded that there is possibility of mid-arousal. In a case in which the determination of S137 changes to YES, the next condition-based determination is further performed.

In Step S138, it is determined whether the epochs n from m=1 to m satisfy a condition "(the average respiratory rate of all the epochs from m=1 to m)$\geq$(the average respiratory rate of all the epochs from n=1 to n=nmax)*mq", where mq is a constant satisfying mq>1. The respiratory rate during an aroused state is generally considered to be higher than that during sleep, and therefore, in a case in which the average respiratory rate of the epochs m=1 to m is greater than mq times the average respiratory rate of the epochs from n=1 to n=nmax including sleep periods, it can be determined that the epochs n from m=1 to m are aroused states.

If the above condition is not satisfied, it is considered that there is no possibility of mid-arousal having happened during the epochs from m=1 to m, and the determination of Step S138 changes to NO, and in Step S140, the consecutive number is initialized to 0 (m=0). In a case in which the condition is satisfied (Step S138 is YES), each epoch n is redefined and stored in memory storage device 9 as an aroused period in Step S139. In Step S140, the consecutive number is initialized to m=0. In Step S141, it is determined whether the second mid-arousal determination is performed for all the epochs nmax. In the case in which the determination on all the epochs is not finished, the determination changes to NO to repeat the steps from Step S132. In a case in which the determination has been made for all the epochs, the determination of Step S140 changes to YES, and the routine then returns to the flowchart of FIG. 16.

Figure 18:
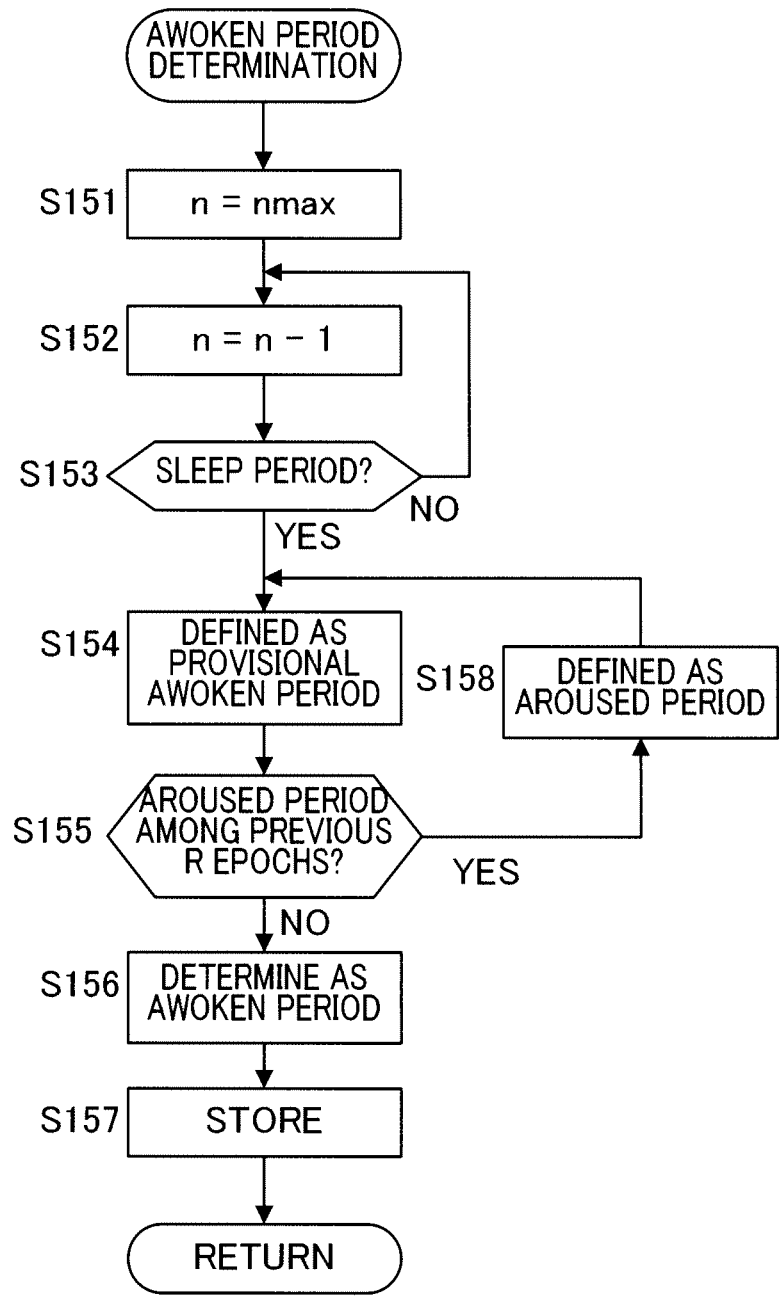
FIG. 18 is a flowchart showing a flow of an awoken period determination process.

The flowchart of FIG. 18 is next referred to in order to describe a process performed by awoken period determiner 18. In Step S151, the epoch is set as n=nmax, and in Step S152, the epoch n is set backward by one epoch with n=n−1, and data corresponding to the subject epoch n is read. In Step S153, it is determined whether the subject epoch n has been determined as a sleep state, i.e., whether the epoch n corresponds to either one of a deep sleep period, a light sleep period, and a REM sleep period (hereinafter referred to as a "sleep period"). In a case in which the epoch n does not correspond to a sleep period, the determination changes to NO. The routine then returns to Step S152, in which the epoch n is decremented by 1 with n=n−1, and the detection of a sleep period is repeated. In a case in which the epoch n corresponds to a sleep period, the determination changes to YES, and in Step S154, the epoch n is defined as a provisional awoken period. In the following Step S155, it is determined whether there is any aroused period in any of previous plural epochs extending back by a certain number of epochs R. Because there should be no aroused period during a certain time period before waking up in normal sleep, the certain number of epochs R corresponds to the certain time period. In a case in which an aroused period is detected among the R number of previous epochs, the determination changes to YES. In Step S158 each of the epochs from detected aroused period to the provisional wake period is defined as an aroused period. In Step S154, an epoch immediately previous to the detected aroused period is redefined as a provisional awoken period. The certain number of epochs R is then defined again in Step S155. In Step S155, the determination changes to NO in a case in which there is no aroused period during the previous R number of epochs, in which case the provisional awoken period is determined as an awoken period in Step S156. In Step S157, the result of determination is stored in association with the subject epoch n in memory storage device 9, and the routine then returns to the flowchart of FIG. 3 showing the main operation.

Figure 29:
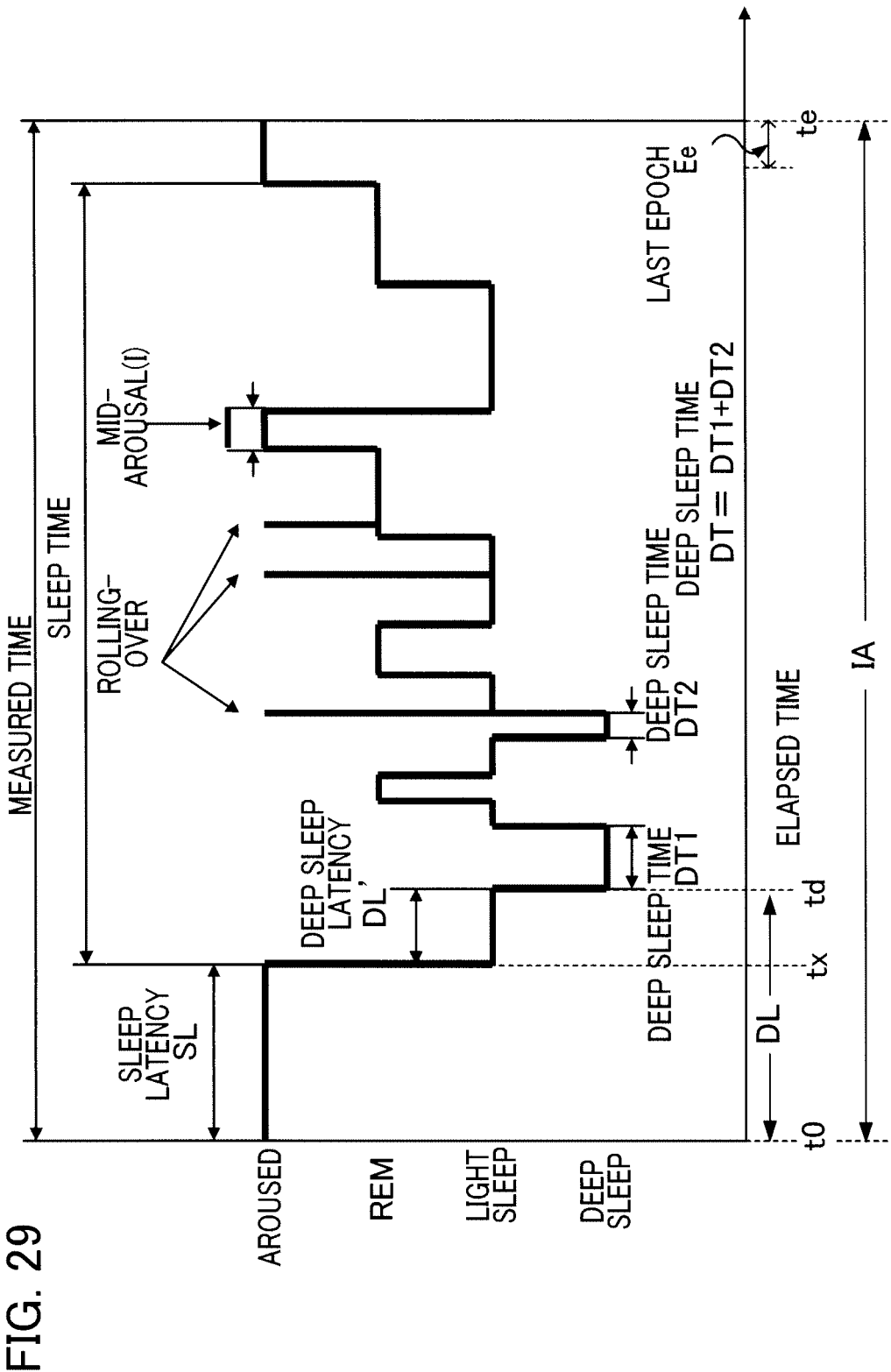
FIG. 29 is a time chart for describing primary parameters.

Subsequently, CPU 6 then proceeds to Step S6 of FIG. 3 to execute the sleep score computation process. In the sleep score computation process, a sleep score (or a sleep index) indicating a degree of the quality of sleep is computed, the sleep score being a comprehensive index of the quality of sleep. As shown in FIG. 29, primary parameters such as sleep latency, deep sleep latency, deep sleep time, number of mid-arousals, number of times the subject rolls over (or the number of times there is movement), and sleep efficiency are obtained by determining sleep stages such as the above described aroused, REM sleep, light sleep, and deep sleep stages during sleep since the subject being examined lies down on the bed until the subject gets up from the bed. Each of these primary parameters alone can be used for evaluating the quality of sleep to some degree of precision.

The evaluation using a single parameter, however, is a mere representation of a portion of various states of sleep. For example, long deep sleep time means that the quality of sleep is high, but in a case in which sleep latency is long even if deep sleep time is long, it may have taken the subject a long time to fall asleep. Therefore, an evaluation focusing merely on deep sleep time cannot lead to comprehensive evaluation of sleep. Taking the above into consideration, in the present embodiment, a secondary parameter is selected in accordance with a principal component analysis to obtain sleep scores functioning as sleep indices.

In the first step, plural primary parameters are measured for a certain population. In this example, the primary parameters include six types of parameters: sleep latency, deep sleep latency, deep sleep time, movement number, and sleep efficiency.

In the second step, correlation coefficients of the plural primary parameters are computed, and a correlation matrix is obtained. The correlation matrix based on the six primary parameters is obtained by the following determinant shown in the following Equation (1), where r11 to r66 are correlation coefficients.

$$\begin{vmatrix} r11 & r12 & r13 & r14 & r15 & r16 \\ r21 & r22 & r23 & r24 & r25 & r26 \\ r31 & r32 & r33 & r34 & r35 & r36 \\ r41 & r42 & r43 & r44 & r45 & r46 \\ r51 & r52 & r53 & r54 & r55 & r56 \\ r61 & r62 & r63 & r64 & r65 & r66 \end{vmatrix} \quad \text{Equation (1)}$$

In the third step, the first to sixth principal components Z1 to Z6 and eigenvectors a11 to a66 are computed based on the correlation matrix and are expressed as in the following Equations (2) to (7):

$$Z1 = a11X1 + a12X2 + a13X3 + a14X4 + a15X5 + a16X6 \quad \text{Equation (2);}$$

$$Z2 = a21X1 + a22X2 + a23X3 + a24X4 + a25X5 + a26X6 \quad \text{Equation (3);}$$

$$Z3 = a31X1 + a32X2 + a33X3 + a34X4 + a35X5 + a36X6 \quad \text{Equation (4);}$$

$$Z4 = a41X1 + a42X2 + a43X3 + a44X4 + a45X5 + a46X6 \quad \text{Equation (5);}$$

$$Z5 = a51X1 + a52X2 + a53X3 + a54X4 + a55X5 + a56X6 \quad \text{Equation (6); and}$$

$$Z6 = a61X1 + a62X2 + a63X3 + a64X4 + a65X5 + a66X6 \quad \text{Equation (7),}$$

where X1 to X6 are the above six primary parameters. The eigenvectors a11 to a66 are determined so that the first to sixth principal components Z1 to Z6 are orthogonal to one another. To be orthogonal to one another means that the principal components are independent of one another, and there are no correlations therebetween.

In the fourth step, it is determined whether the eigenvectors a11 to a66 each reflect the meaning of the first to six principal components Z1 to Z6. It is for example assumed that X1 is sleep latency and that a11>0 and a21<0 are satisfied. In this case, a value of the first principal component Z1 increases as a value of X1 increases, which means that the degree of the quality of sleep is improved, whereas a value of the second principal component Z2 decreases as a value of X1 increases, which means that the degree of the quality of sleep is degraded. Thus, the degree of the quality of sleep is not accurately reflected. This is because the selection of the primary parameter X1 is not appropriate. In such a case, the selected data set of the primary parameters is abandoned, and another data set of the primary parameters is selected.

In the fifth step, eigenvalues λ1 to λ6 of the first to six principal components Z1 to Z6 are obtained based on the following matrix.

$$\begin{vmatrix} r11-\lambda 1 & r12 & r13 & r14 & r15 & r16 \\ r21 & r22-\lambda 2 & r23 & r24 & r25 & r26 \\ r31 & r32 & r33-\lambda 3 & r34 & r35 & r36 \\ r41 & r42 & r43 & r44-\lambda 4 & r45 & r46 \\ r51 & r52 & r53 & r54 & r55-\lambda 5 & r56 \\ r61 & r62 & r63 & r64 & r65 & r66-\lambda 6 \end{vmatrix} = 0 \quad \text{Equation (8)}$$

The eigenvalues λ1 to λ6 relate to the variances of the first to sixth principal components Z1 to Z6. The variance of a principal component becomes smaller as the eigenvalue thereof becomes smaller. As the variance becomes larger, the importance of the corresponding principal component increases. That is, the contribution of a principal component is higher as its eigenvalue becomes larger.

In the sixth step, the contribution ratios of the first to the sixth principal components are calculated. The contribution ratio is a ratio of an eigenvalue of each principal component to the sum of the eigenvalues of all the principal components. In a case in which the eigenvalues have been calculated based on a coefficient matrix, the contribution ratio is obtained by dividing each of the eigenvalues λ1 to λ6 by the total number 6 of the principal components.

In the seventh step, the contribution ratios of the first to the sixth principal components Z1 to Z6 are added up in order of decreasing contribution ratios to a point where the cumulative contribution ratio exceeds 0.8. It is then decided that the principal components up to the point will be used as secondary parameters. For example, in a case in which the analysis of the principal components are given as shown in the following table, and when K3<0.8<K4, the first to the fourth parameters will be used as the secondary parameters.

|  | First Principal Component | Second Principal Component | Third Principal Component | Fourth Principal Component | Fifth Principal Component | Sixth Principal Component |
| --- | --- | --- | --- | --- | --- | --- |
| eigenvalue | λ1 | λ2 | λ3 | λ4 | λ5 | λ6 |
| contribution ratio | k1 | k2 | k3 | k4 | k5 | k6 |

-continued

|  | First Principal Component | Second Principal Component | Third Principal Component | Fourth Principal Component | Fifth Principal Component | Sixth Principal Component |
|---|---|---|---|---|---|---|
| cumulative contribution ratio | K1 | K2 | K3 | K4 | K5 | 1 |

In the eighth step, the square root of the eigenvalues is multiplied with the eigenvectors, to obtain factor loadings, and those having values equal to or below a predetermined reference value (e.g., 0.5) are deleted. It is to be noted that the factor loadings need not be necessarily deleted.

After four secondary parameters are selected by performing the above first to the eighth steps, Equations (14) to (17) that will be described below are derived.

The four secondary parameters are obtained by multiplying the six primary parameters X1 to X6 respectively by first coefficients a11 to a46 and adding up the products as shown in Equations (2) to (5). Because the first coefficients a11 to a46 are eigenvectors, the four secondary parameters Z1 to Z4 are linearly independent of one another. In other words, a correlation coefficient between 2 secondary parameters is 0, i.e., r=0. Therefore, a correlation coefficient between any two of the four secondary parameters Z1 to Z4 is smaller than a correlation coefficient between any two of the six primary parameters X1 to X6. Thus, the secondary parameters are the aggregation of the primary parameters from the point of view of sleep, and each secondary parameter simply shows a characteristic of sleep. Therefore, evaluating the secondary parameters enables the generation of a more accurate evaluation index when compared with the evaluation using a single primary parameter or a random combination of the primary parameters.

Figure 19:
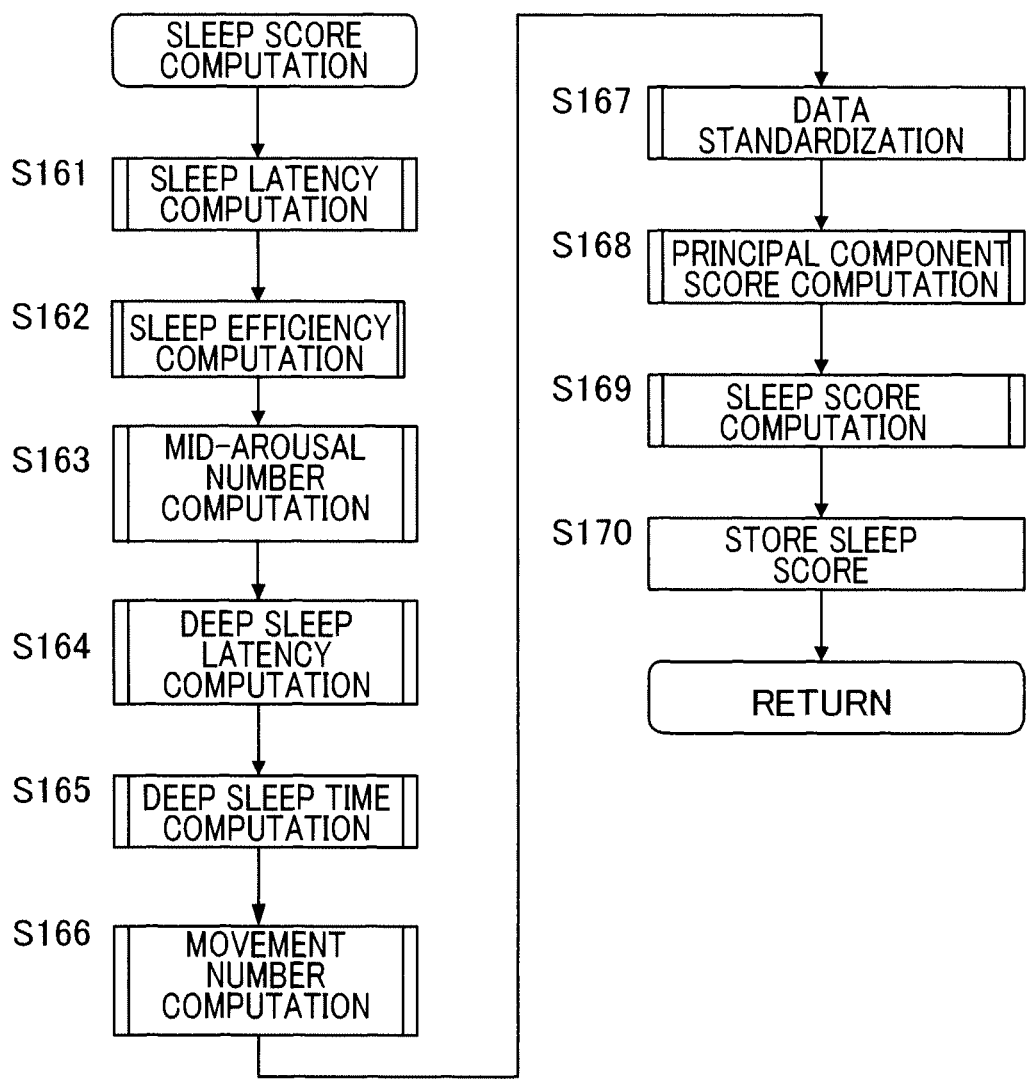
FIG. 19 is a flowchart showing a flow of a sleep score computation process.

FIG. 19 is a flowchart showing a flow of plural computation processes performed in the sleep score computation process, and FIGS. 20 to 28 are flowcharts each showing a detailed flow of each computation process. FIG. 29 is a time chart for describing parameters computed in the sleep score computation process. In the following, it is assumed that CPU 6 executes these processes in accordance with a predetermined program.

The sleep score computation process is performed after the subject being examined has reached full wakefulness (i.e., after the subject being examined has gotten out of bed). A state of full wakefulness may be detected in a case in which a state in which the breathing of the subject being examined is not detected and this persists for a predetermined period. Alternatively, a state of full wakefulness may be detected in a case in which, by providing a measurement start or end button (not shown), the end button is depressed. There are stored in memory storage device 9 data of a state of the subject being examined in each epoch since the start (time t0 of FIG. 29) until the end (time te) of the measurement, for use in the sleep score computation process.

Figure 20:
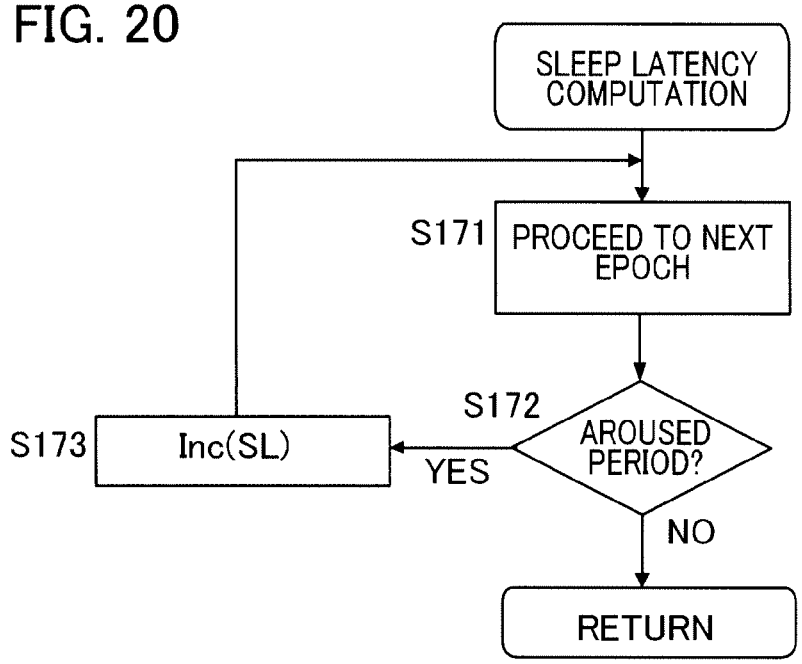
FIG. 20 is a flowchart showing a flow of a sleep latency computation process.

As shown in FIG. 19, a sleep latency computation process (Step S161) is first performed in the sleep score computation process. The subject being examined is in an aroused state in the first epoch after the measurement by sensor unit 2 has started. In the sleep latency computation process, therefore, the routine proceeds to the next epoch in Step S171 as shown in FIG. 20. It is then determined whether the subject epoch is an aroused state (Step S172). In a case in which the determination changes to YES, a value of the sleep latency SL is incremented (Step S173), and the processes of Steps S171 and S172 are repeated. As shown in FIG. 29, the sleep latency SL is the number of epochs required since the subject being examined started the measurement until the subject falls asleep (time tx), and the initial value is set as SL=1. The value of the sleep latency SL is incremented by 1 every time the process of Step S173 is performed and is stored in memory storage device 9. In a case in which the determination of Step S172 changes to NO, the sleep latency computation process ends, and the routine returns to the flowchart of FIG. 19. That is, a resultant value of the sleep latency SL computed last time in Step S173 is stored as the computed value of the sleep latency SL.

Figure 21:
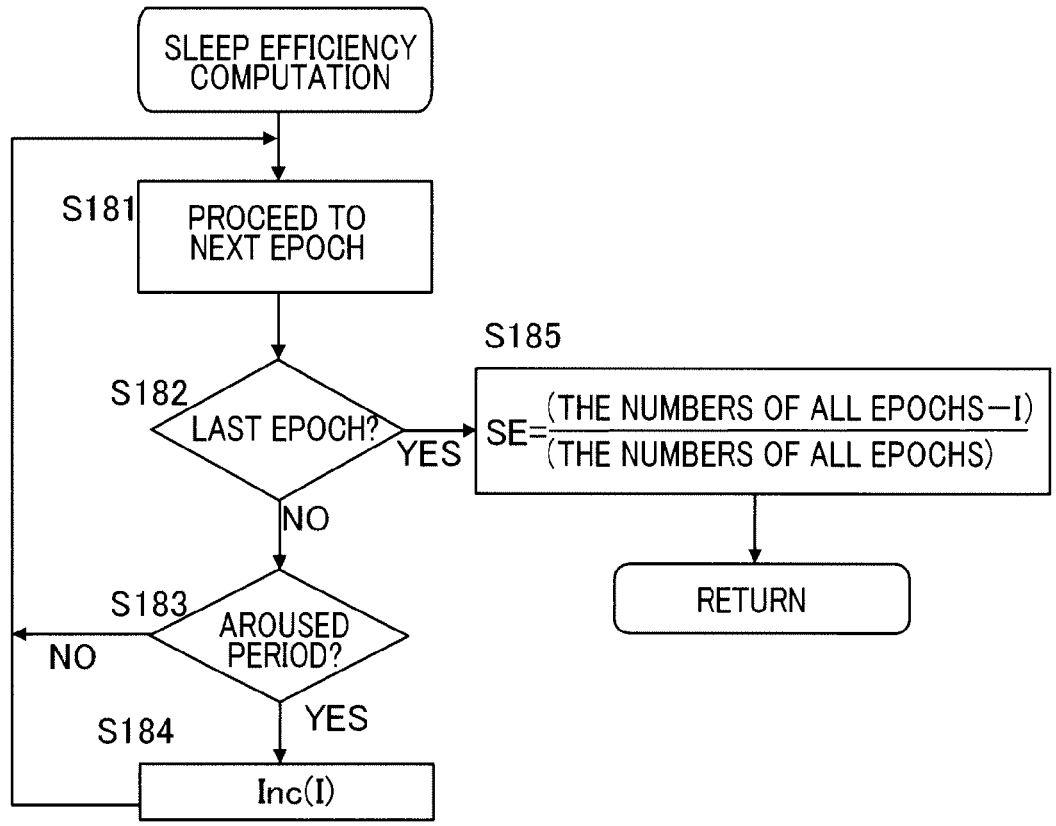
FIG. 21 is a flowchart showing a flow of a sleep efficiency computation process.

Subsequently, CPU 6 proceeds to a sleep efficiency computation process (Step S162), the details of which are shown in FIG. 21. The sleep efficiency SE is a value obtained by (IA−I)/IA, where IA is the total number of the epochs from the start (time t0 of FIG. 29) to the end (time te) of the measurement; and I is the number of epochs (aroused epoch number) that have been determined as aroused states in the following determination step S183. Therefore, in the sleep efficiency computation process, because the first epoch is an aroused state, the aroused epoch number (I) is initially set as 1 and is incremented every time the subject epoch is determined as being an aroused state (Step S184).

As shown in FIG. 21, in Step S181, CPU 6 first advances the epoch to the next epoch. Subsequently, in Step S182, it is determined whether the subject epoch is one that is immediately before changing to full wakefulness, i.e., the last epoch Ee of FIG. 29. In a case in which the determination changes to NO, it is determined whether the epoch is an aroused state (Step S183). In a case in which the determination changes to YES, the routine proceeds to Step S181 in which the value of I is incremented by 1, and the routine proceeds to the next epoch. In a case in which the determination of Step S183 changes to NO, the routine returns to Step S181 without incrementing the value of the aroused epoch number (I). CPU 6 repeats the processes of Steps S181 to S183 or Steps S181 to S184 until the determination of Step S182 changes to YES.

In a case in which the determination of Step S182 is affirmative, the routine proceeds to Step S185 in which the sleep efficiency SE is computed. Specifically, the latest value of the aroused epoch number I and the total number of epochs IA are assigned to the corresponding variables of the above equation SE=(IA−I)/IA, thereby yielding the sleep efficiency SE. The sleep efficiency computation process is then finished, and the routine returns to the flowchart of FIG. 19.

Figure 22:
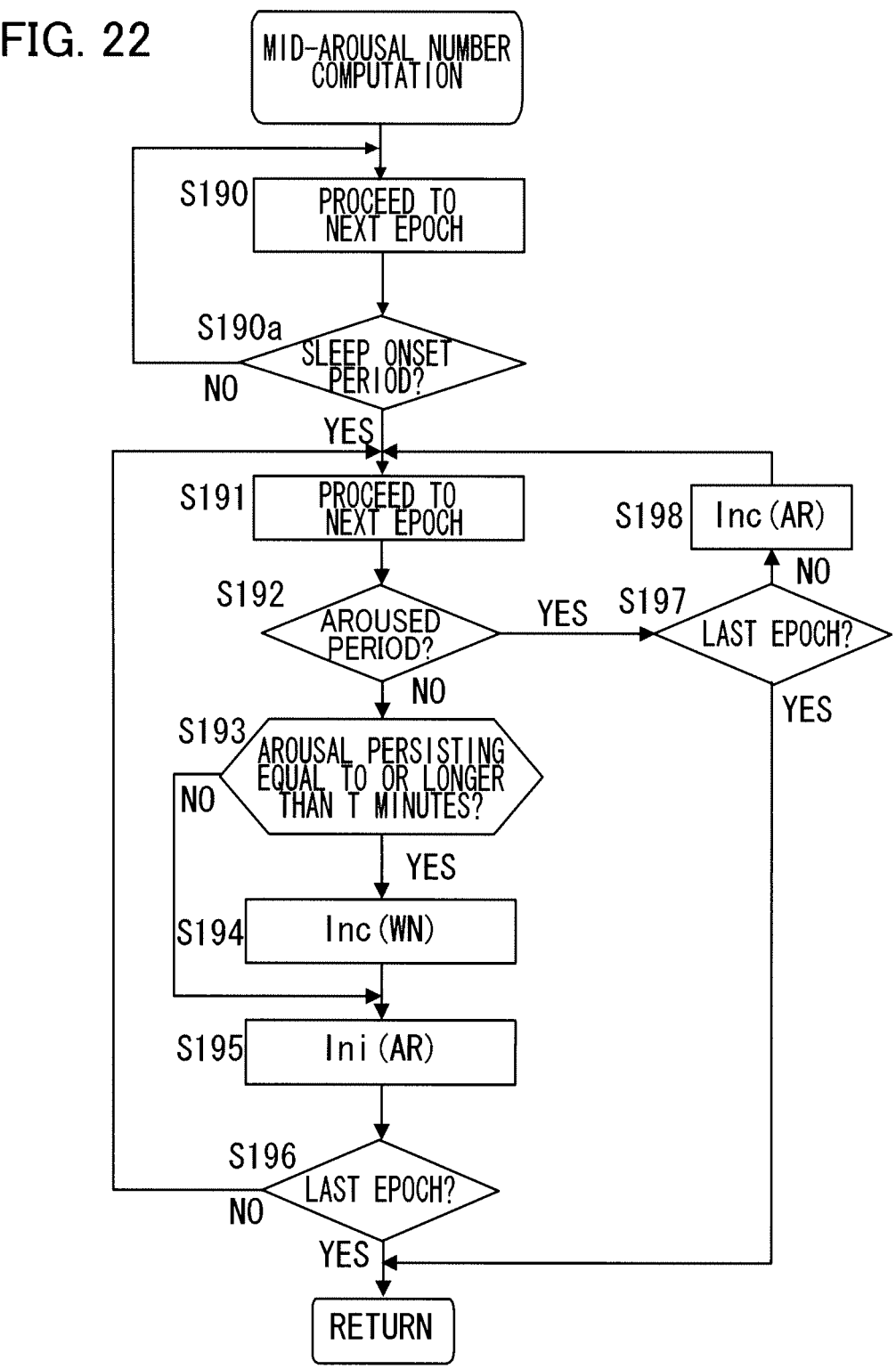
FIG. 22 is a flowchart showing a flow of a process of computing the number of mid-arousals.

Subsequently, CPU 6 executes a mid-arousal number computation process of Step S163. The initial aroused period(s) immediately after lying down and the last aroused period(s) immediately before getting out of bed are not regarded as mid-arousal states. Therefore, as shown in FIG. 22, in the mid-arousal number computation process, CPU 6 first advances the epoch to the next epoch (Step S190), and then in Step S190a, CPU 6 determines whether the subject epoch is the sleep-onset period determined in the sleep-onset period determination process shown in FIGS. 13A and 13B. In a case in which the result of the determination of Step S190a changes to NO, the routine returns to Step S190 to repeat Steps S190 and S190a until the determination of Step S190a changes to YES.

In a case in which the determination of Step 190a changes to YES, the routine proceeds to Step S191 in which the subject epoch is further advanced to the next epoch. Subsequently, in Step S192, it is determined whether the subject epoch is an aroused period. In a case in which a result of the determination changes to YES, CPU 6 then determines whether the subject epoch is the final epoch Ee of FIG. 29 (Step S197). If this determination result changes to NO, i.e., in a case in which the subject epoch is not the last epoch, CPU 6 increments the number of consecutive aroused epochs (AR, where the initial value AR=0) by 1 in Step S198, and the routine returns to Step S191.

In a case in which a result of the determination of Step S192 changes to NO, it is then determined in Step S193 whether the aroused state persists for a period equal to or longer than T minutes. As described above, the duration of 1 epoch is 30 seconds in the present embodiment. It is therefore determined that the subject being examined is in an aroused state in a case in which an aroused epoch continues for 10 or more times in succession if T=5. Therefore, CPU 6 affirms the determination of Step S193 only in a case in which the current value of the number of consecutive aroused epochs AR is equal to or larger than a predetermined number (for example, 10). In a case in which a result of the determination of Step S193 changes to YES, the routine proceeds to Step S194 in which CPU 6 increments the number of mid-arousals (WN, where the initial value WN=0) by 1. Subsequently in Step S195, CPU 6 initializes the value of the number of consecutive aroused epochs AR. CPU 6 then determines whether the subject epoch is the final epoch Ee (Step S196). In a case in which a result of the determination of Step S196 changes to NO, the routine returns to Step S191 until the result of the determination in Step S196 or S197 changes to YES. The mid-arousal number computation process is finished in a case in which a result of the determination in Step S196 or S197 is affirmative. The routine then returns to the flowchart of FIG. 19.

Figure 23:
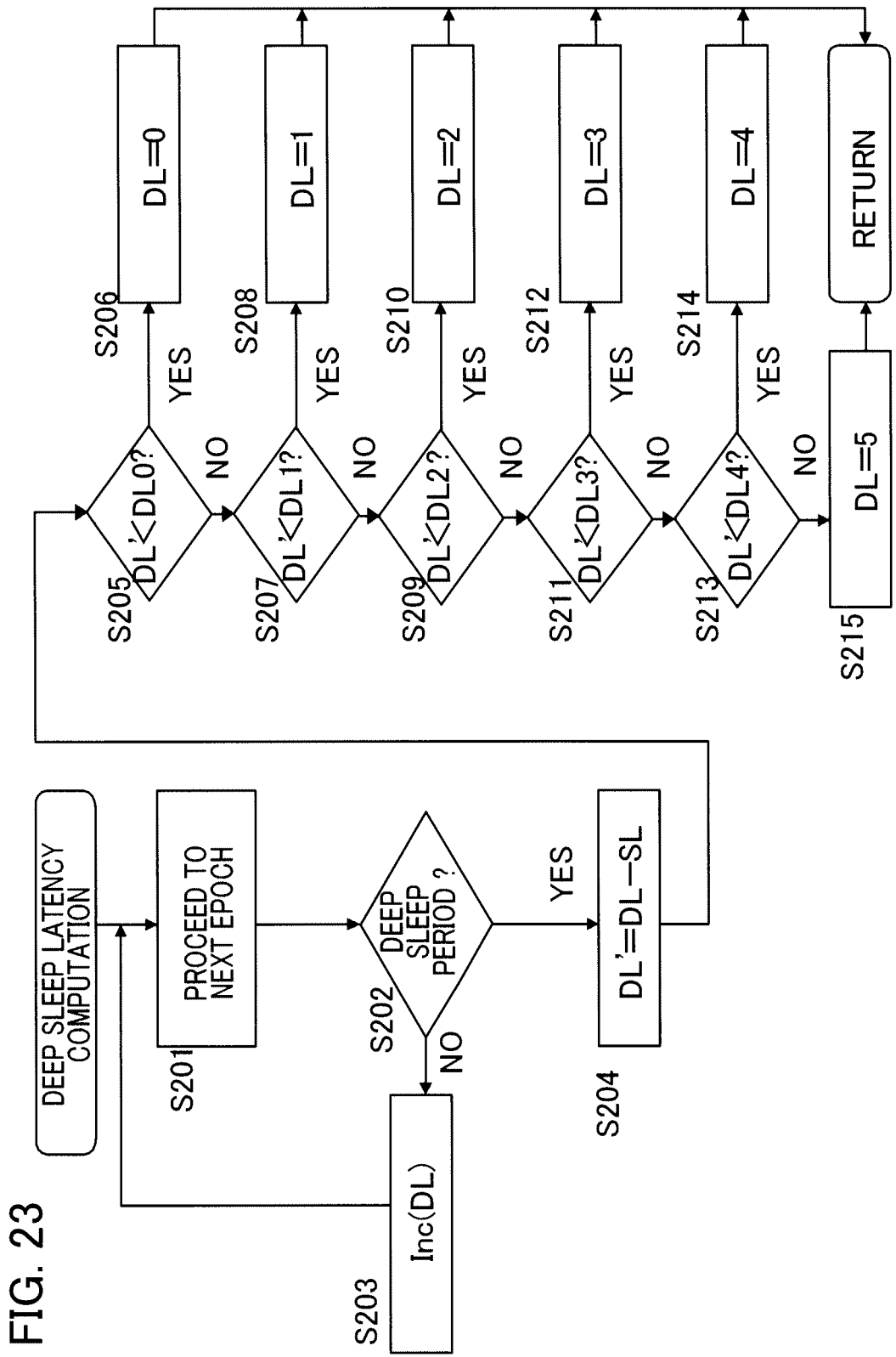
FIG. 23 is a flowchart showing a flow of a deep sleep latency computation process.

CPU 6 then proceeds to a deep sleep latency computation process (Step S164) of FIG. 19, the details of which are shown in the flowchart of FIG. 23. As shown in FIG. 23, in the deep sleep latency computation process, CPU 6 first advances the subject epoch to the next epoch in Step S201. In Step S202, it is determined whether the subject epoch is a deep sleep state. In a case in which a result of the determination is negative, the routine proceeds to Step S203 in which a value of the deep sleep latency DL is incremented by 1, where the initial value of DL is 0. The deep sleep latency DL indicates the number of epochs required since the measurement started (time t0 of FIG. 29) until the subject being examined transitions to a deep sleep state (time td).

On the other hand, in a case in which a result of the determination of Step S202 is affirmative, CPU 6 executes DL'=DL−SL to obtain the number of epochs DL' required since the start of the transition from the sleep latency to a deep sleep state (time tx of FIG. 29) to a deep sleep state (time td). In Step S205, in a case in which DL'<DL0 is true, the deep sleep latency DL is determined to be 0, i.e., DL=0, in Step S206, where DL0 is a predetermined reference value. In a case in which DL'<DL0 is not true, it is determined in Step S207 whether DL'<DL1 is true. In a case in which a result of the determination is affirmative, it is determined that DL is 1 (DL=1), whereas in a case in which the result of the determination is negative, the routine proceeds to Step S209. The values of deep sleep latency DL are determined to be one of 2 to 5 based on the value of DL' and each reference value DL0 to DL4 (Steps S209 to S215). In a case in which the value of the deep sleep latency DL is determined, the routine returns to the flowchart of FIG. 19.

Subsequently, CPU 6 executes a deep sleep time computation process of Step S165. The deep sleep time DT is the total number of epochs that are deep sleep periods since the start until the end of the measurement (time t0 to te) as shown in FIG. 29. Therefore, in a case in which deep sleep time DT1 and D2 are detected during a period from time t0 to te as shown in FIG. 29, the deep sleep time is DT=DT1+DT2.

Figure 24:
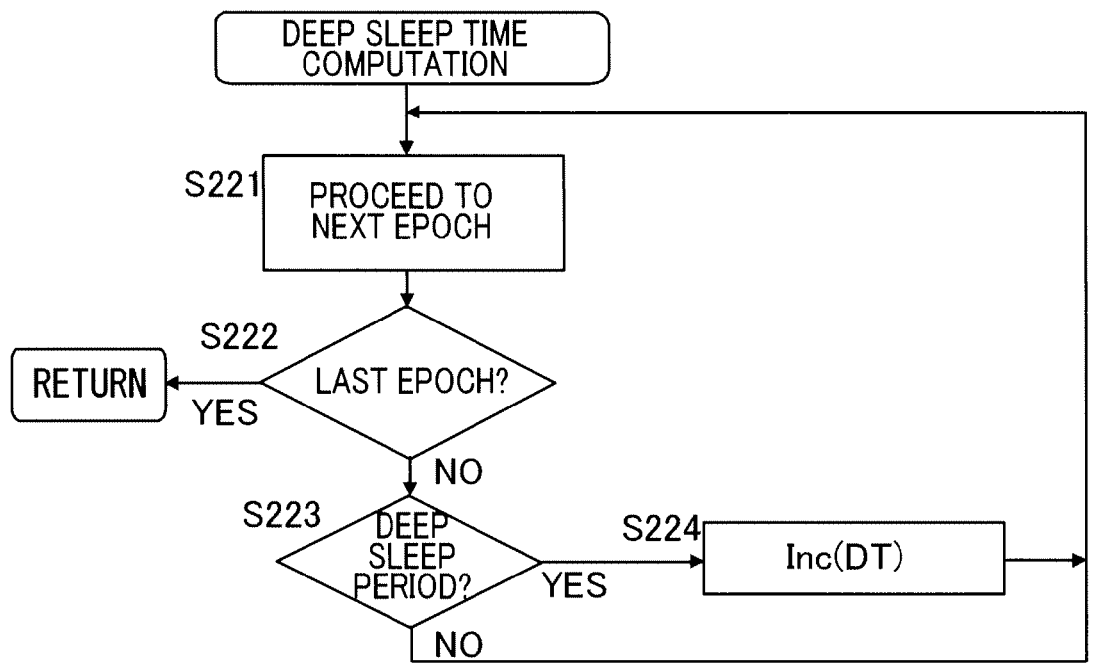
FIG. 24 is a flowchart showing a flow of a deep sleep time computation process.

As shown in FIG. 24, in the deep sleep time computation process, CPU 6 advances the epoch to the next epoch (Step S221). Subsequently, in Step S222, it is determined whether the subject epoch is the final epoch Ee. In a case in which a result of the determination changes to NO, it is then determined whether the subject epoch is a deep sleep state. In a case in which the determination of Step S223 is YES, i.e., in a case in which the subject epoch is a deep sleep state, the determination changes to YES. Then in Step S224, the deep sleep time DT is incremented by 1, where the initial value of DT is 0, and the routine returns to Step S221. On the other hand, in a case in which the determination of Step S223 changes to NO, the routine returns to Step S221 without incrementing the value of the deep sleep time DT. CPU 6 repeats the processes of Steps S221 to S224 or the processes of Steps S221 to 223 until the result of the determination of Step S222 changes to YES. Once the result of the determination of Step S222 changes to YES, the routine returns to the process shown in the flowchart of FIG. 19.

Figure 25:
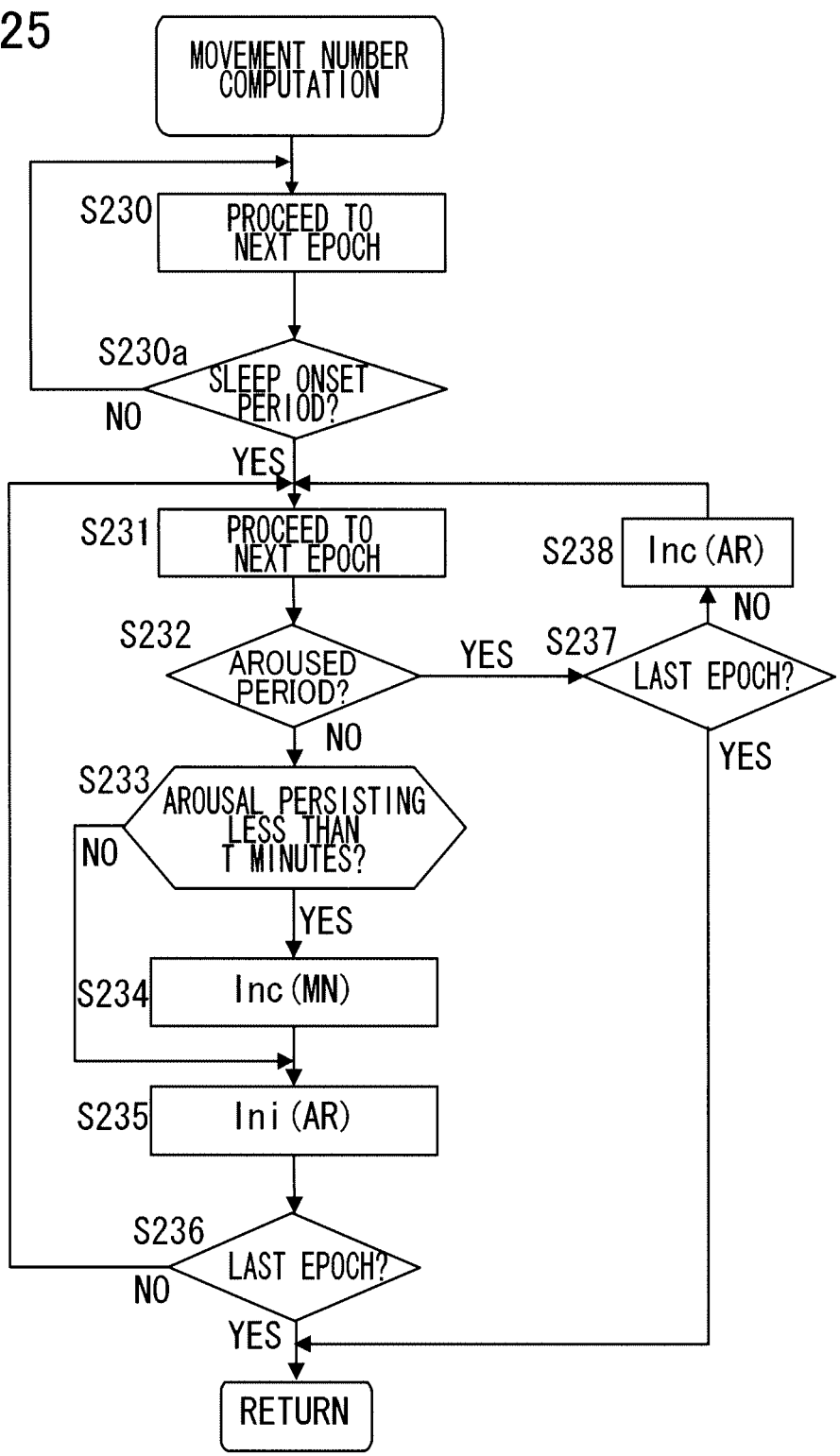
FIG. 25 is a flowchart showing a flow of a process of computing the number of movements or number of time the subject rolled over.

CPU 6 subsequently executes a movement number (the number of times the subject rolled over) computation process of Step S165. As shown in FIG. 25, in the movement number computation process, CPU 6 starts with the first epoch and then advances the subject epoch to the next epoch (Step S230), and then in Step S230a, CPU 6 determines whether the subject epoch is the sleep-onset period determined in the sleep-onset period determination process shown in FIGS. 13A and 13B. In a case in which the result of the determination of Step S230a changes to NO, the routine returns to Step S230 to repeat Steps S230 and S230a until the determination of Step S230a changes to YES.

In a case in which the determination of Step 230a changes to YES, the routine proceeds to Step S231 in which the subject epoch is further advanced to the next epoch. Subsequently, in Step S232, it is determined whether the subject epoch is an aroused period. In a case in which a result of the determination changes to YES, CPU 6 then determines whether the subject epoch is the final epoch Ee of FIG. 29 (Step S237). If this determination result changes to NO, i.e., in a case in which the subject epoch is not the last epoch, CPU 6 increments the number of consecutive aroused epochs (AR, where the initial value AR=0) by 1 in Step S238, and the routine returns to Step S231.

In a case in which a result of the determination of Step S232 changes to NO, it is then determined in Step S233 whether the aroused state continues for less than T minutes. As described above, because one epoch corresponds to 30 seconds (1 epoch=30 sec), it is determined that there is a rolling-over movement in a case in which the number of continuous aroused epochs is less than 3 if T=1.5. CPU 6 therefore affirms the determination of Step S233 only in a case in which the value of the number of continuous aroused epochs AR is less than the predetermined number (for example, 3). The routine then proceeds to Step S234, in which the number of movements (MN, where the initial value MN=0) is incremented by 1. In Step S235, CPU 6 initializes the value of the number of consecutive aroused epochs AR. CPU 6 then determines whether the subject epoch is the final epoch Ee (Step S236). In a case in which result of the determination of Step S236 changes to NO, the routine returns to Step S231 to repeat the processes of Steps S231 to S235 until the result of the determination in Step S236 or S237 changes to YES. The movement number computation process is finished in a case in which a result of the determination in Step S236 or S237 is affirmative. The routine then returns to the flowchart of FIG. 19.

Figure 26:
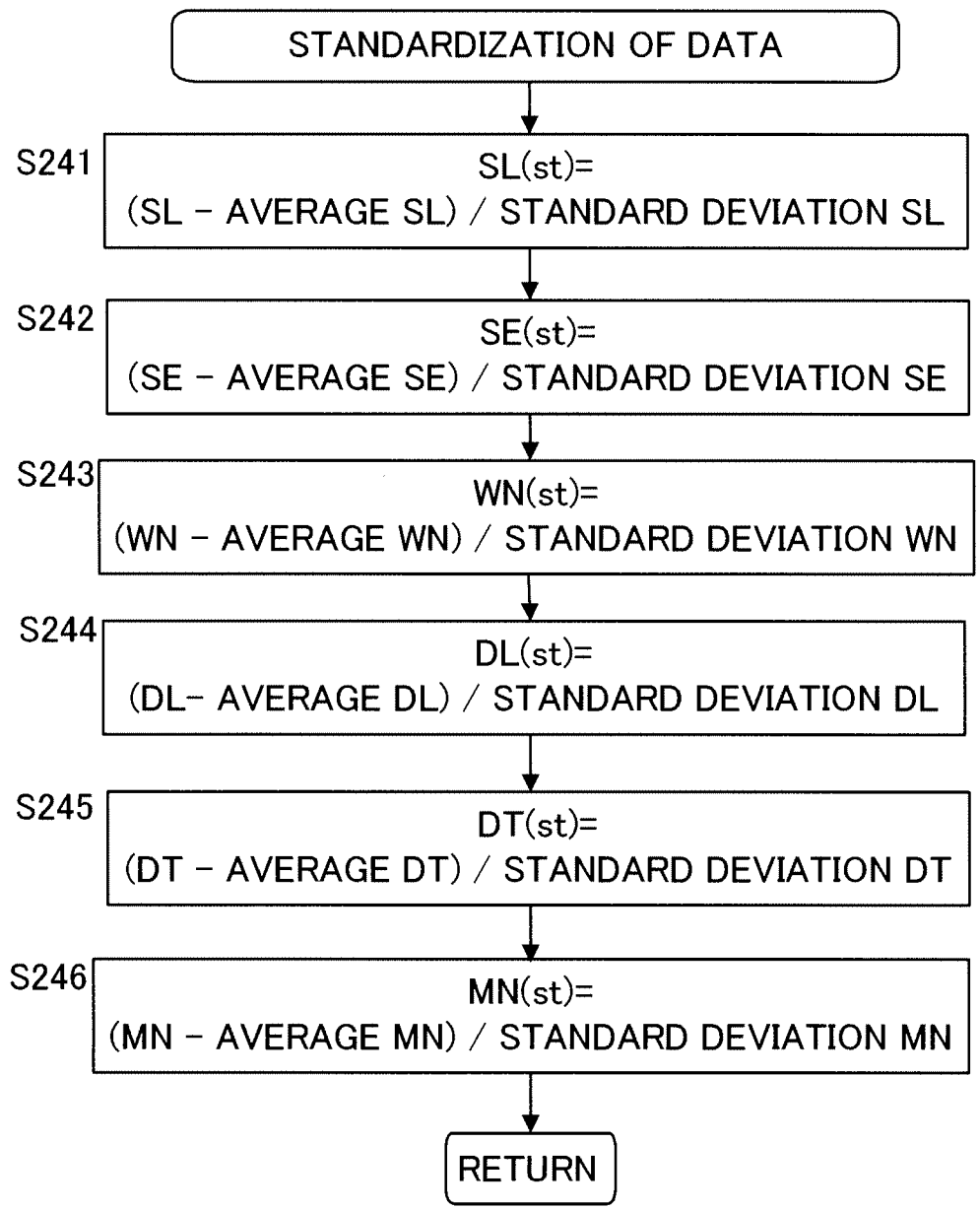
FIG. 26 is a flowchart showing a flow of a process of standardizing data.

CPU 6 then executes a standardization process of each data in Step S167 of FIG. 19. As shown in FIG. 26, in the data standardization process, each parameter value (raw data) obtained respectively in the above Steps S161 to S166 is standardized. In Step S241, the standard value SL(st) of sleep latency SL is obtained by SL(st)=(SL−average SL)/standard deviation SL. The average SL is the average value (fixed value) of the sleep latency SL in a population, and the standard deviation SL is the standard deviation (fixed value) thereof. The population is, for example, a group of X number of humans in their twenties in a case in which the age of the subject being examined is in twenties. The subject being examined uses operation unit 5 to enter the parameters of the subject, such as the age and sex in advance, whereby CPU 6 is enabled to select data of an appropriate population, to use the selected data in the standardization process. The data of different groups of populations is stored in advance in memory storage device 9. CPU 6 executes the computation of Step S241 by reading the average value and the standard deviation from memory storage device 9.

Likewise, in each process of Steps S242 to S246, the standardization process of each parameter is performed. The standard value of each parameter is obtained through each of the following Equations (9) to (13):

Sleep Efficiency SE(st)=(SE−Average SE)/Standard Deviation SE      Equation (9);

Mid-arousal number WN(st)=(WN−Average WN)/ Standard Deviation WN      Equation (10);

Deep Sleep Latency DL(st)=(DL−Average DL)/Standard Deviation DL      Equation (11);

Deep Sleep Time DT(st)=(DT−Average DT)Standard Deviation DT      Equation (12); and Movement Number MN(st)=(MN−Average MN)/ Standard Deviation MN      Equation (13).

The average and the standard deviation are obtained for each parameter in the same way as described above for the sleep latency SL. Also, data of a population group corresponding to the parameters of the subject being examined is also selected in the same way as above.

Without the standardization process, the sleep latency SL, the sleep efficiency SE, the mid-arousal number WN, the deep sleep latency DL, the deep sleep time DT, and the movement number MN could not be treated in the same process because they are in different units. When the process of Step S246 is finished, the routine returns to the flowchart of FIG. 19.

Figure 27:
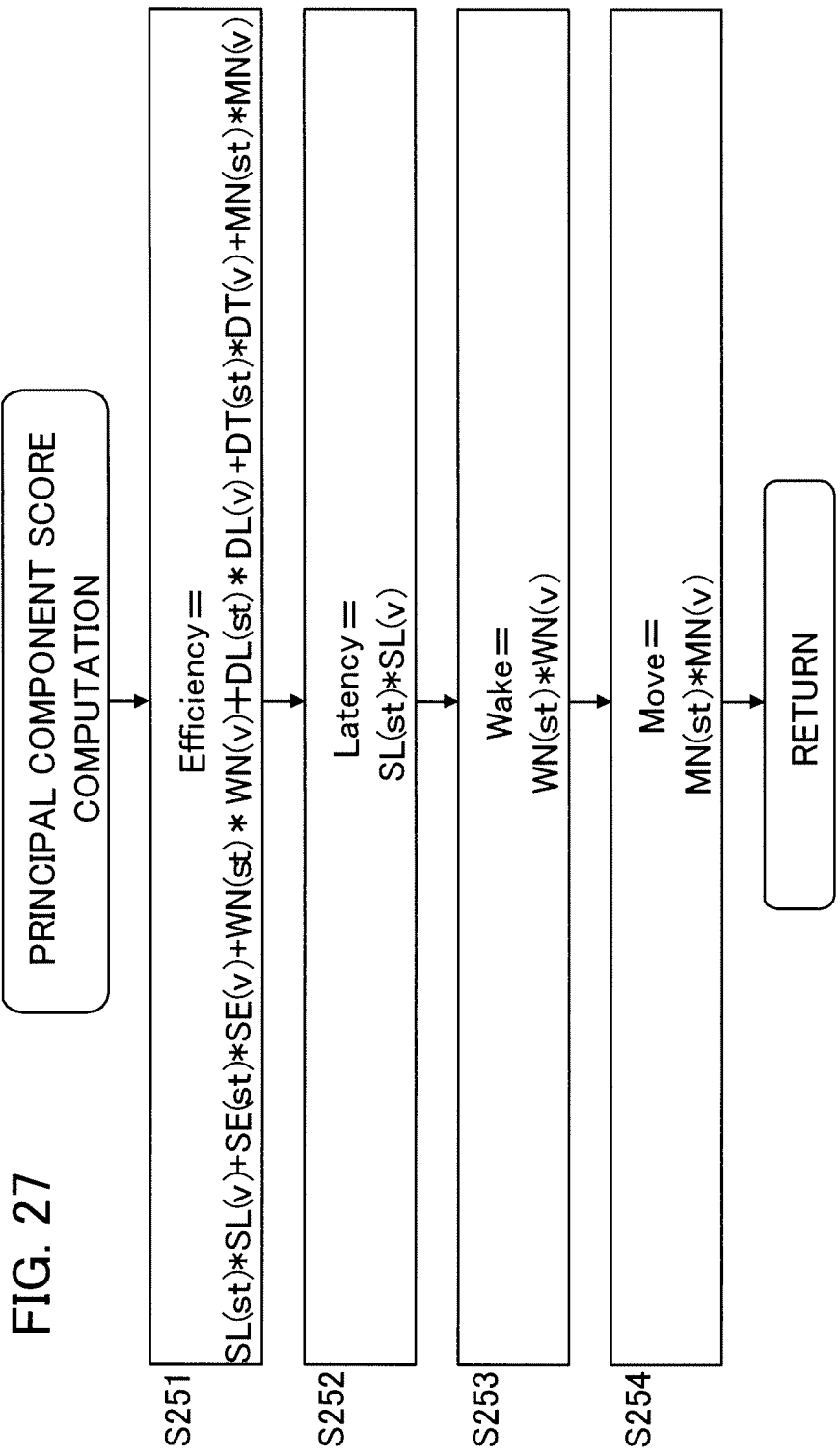
FIG. 27 is a flowchart showing a flow of a principal component score computation process.

CPU 6 then executes a principal component score computation process of Step S168. As shown in FIG. 27, in the principal component score computation process, the standard values of each parameter obtained in the above Step S167 are used for computation. In the principal component score computation process, the six primary parameters, the sleep latency SL, the sleep efficiency SE, the mid-arousal number WN, the deep sleep latency DL, the deep sleep time DT, and the movement number MN, are used to compute the four secondary parameters, efficiency (Efficiency), sleep onset latency (Latency), mid-arousal (Wake), and movements or number of times the subject rolled over (Move).

CPU 6 computes efficiency (Efficiency), sleep onset latency (Latency), mid-arousal (Wake), and movements (Move) in accordance with Equations (14) to (17) (Steps S251 to S254):

Efficiency={SL(st)*SL(v)}+{SE(st)*SE(v)}+{WN(st) *WN(v)}+{DL(st)*DL(v)}+{DT(st)*DT(v)}+ {MN(st)*MN(v)}      Equation (14);

Latency=SL(st)*SL(v)      Equation (15);

Wake=WN(st)*WN(v)      Equation (16); and

Move=MN(st)*MN(v)      Equation (17), where SL(v), SE(v), WN(v), DL(v), DT(v), and MN(v) are eigenvectors (first coefficients), are fixed values obtained through the principal component analysis of a population group, and are stored in memory storage unit 9. CPU 6 reads the fixed values from memory storage unit 9 to perform the computation processes of Steps S251 to S254.

Figure 28:
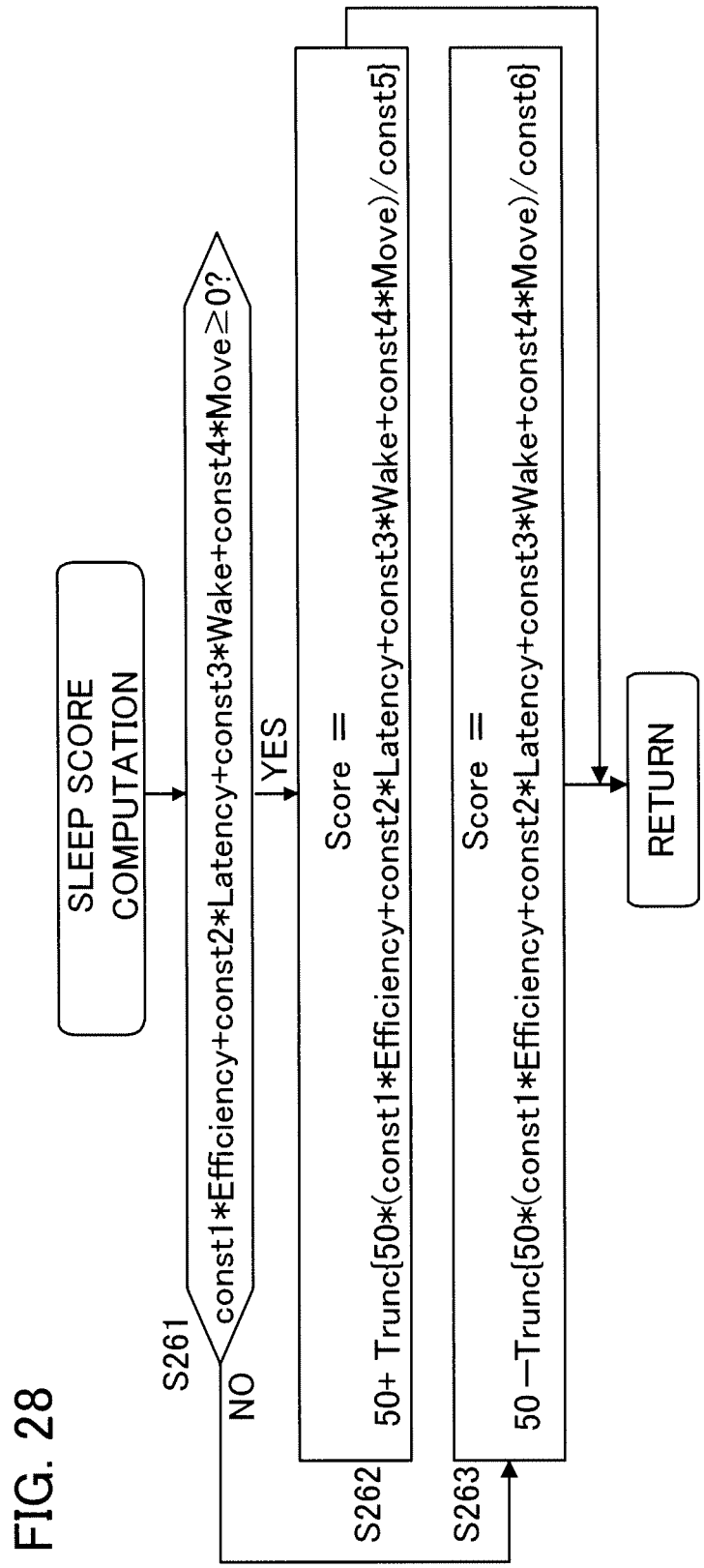
FIG. 28 is a flowchart showing a flow of a sleep score computation process.

CPU 6 then executes a sleep score computation process of Step S169, the details of which are shown in FIG. 28. CPU 6 first determines whether const1*Efficiency+ const2*Latency+const3*Wake+const4*Move≥0 is true (Step S261), where the constants: const1, const2, const3, and const4 (second coefficients) are fixed values obtained through the principal component analysis of a population group. For example, each of the constants may be a value obtained by multiplying the first coefficient by the square root of an eigenvalue.

In a case in which a result of the determination of Step S261 is affirmative, CPU 6 proceeds to Step S262, in which a sleep score (Score) is computed in accordance with the following equation (Step S262).

Score=50+Trunc[50*{(const1*Efficiency)+ (const2*Latency)+(const3*Wake)+ (const4*Move)}/const5]      Equation (18)

On the other hand, in a case in which a result of the determination of Step S261 is negative, CPU 6 advances the routine to Step S263, in which a sleep score (Score) is computed in accordance with the following equation (Step S263).

Score=50−Trunc[50*{(const1*Efficiency)+ (const2*Latency)+(const3*Wake)+ (const4*Move)}/const6]      Equation (19)

In Equation (18), const5 is a value set as the maximum value of sleep scores (Score), and in Equation (19), const6 is a value set as the minimum value of sleep scores (Score). These fixed values are stored in memory storage device 9, and CPU 6 reads them for use in computation.

CPU 6 stores sleep score (Score) obtained in Step S262 or S263 in memory storage device 9 (Step S170 of FIG. 19). CPU 6 then proceeds to Step S7 of FIG. 3 to execute the evaluation result display process.

Figure 30:
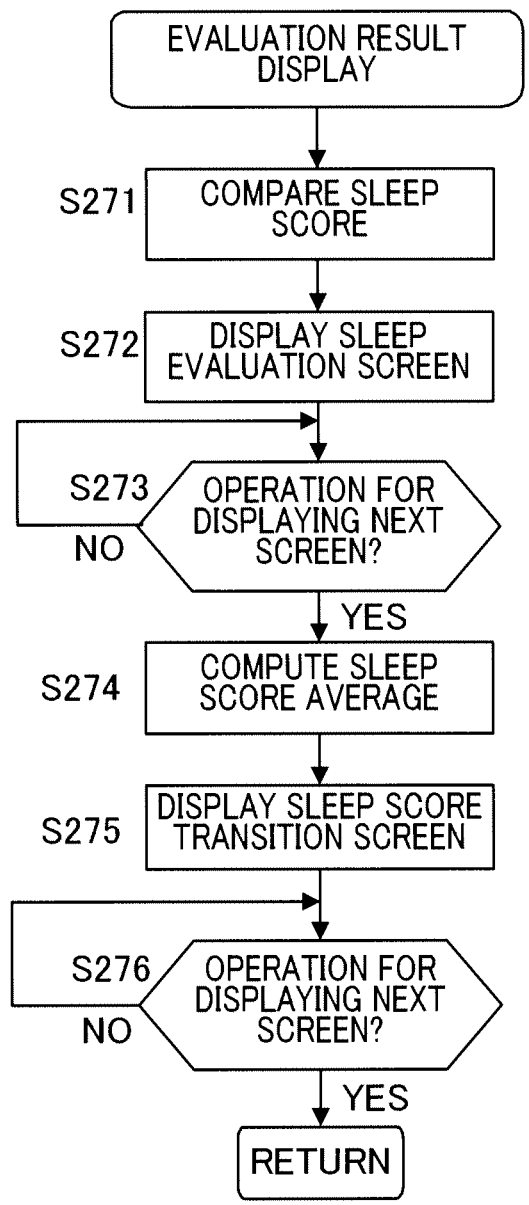
FIG. 30 is a flowchart showing a flow of displaying a result of the determination.
Figure 31:
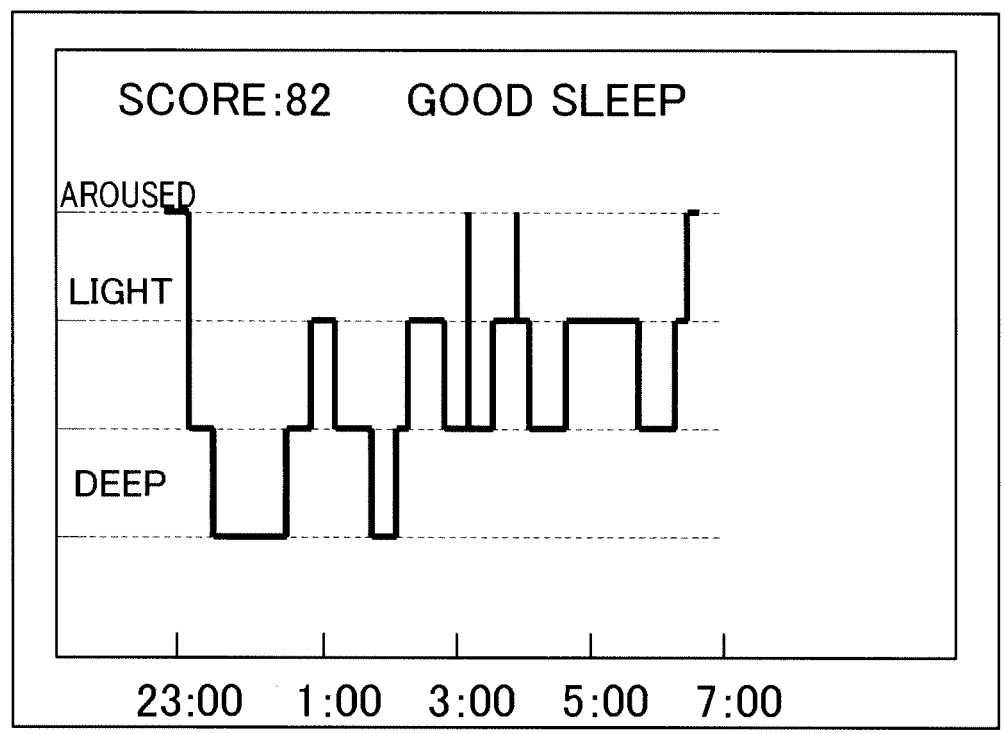
FIG. 31 is a diagram showing an example of a display showing a result of the determination.
Figure 32:
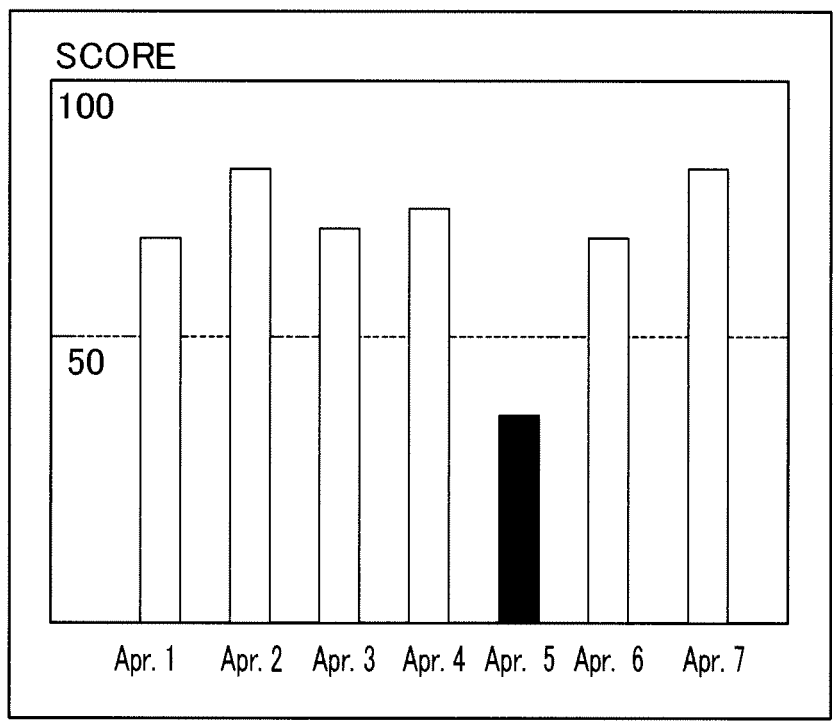
FIG. 32 is a diagram showing another example of a display showing a result of the determination.

FIG. 30 is a flowchart showing the details of the evaluation result display process executed by CPU 6, FIG. 31 is an example of an evaluation display screen, and FIG. 32 is an example of a sleep score change screen.

CPU 6 first executes a sleep score comparison process (Step S271). In this sleep score comparison process, sleep scores (Score) obtained by the sleep score computation process are compared with a first reference value and a second reference value, so as to categorize the sleep scores (Score) into three categories (or parts). Specifically, a sleep score (Score) is categorized into a first category in a case in which the score is equal to or less than the first reference value W; a sleep score (Score) is categorized into a second category in a case in which the score exceeds the first reference value W and is equal to or less than the second reference value Y, and a sleep score (Score) is categorized into a third category in a case in which the score exceeds the second reference value Y, where the first reference value W is the addition of the average and the variance of sleep scores of a group of people having sleep disorders and the second reference value Y is the addition of the average and the variance of sleep scores of a group of people having normal sleep. The fixed values W and Y are stored in memory storage device 9 and are read for use in the sleep score comparison process.

CPU 6 then displays a message "BAD SLEEP" in a case in which the sleep score (Score) is categorized into the first category, displays a message "NORMAL SLEEP" in a case in which the sleep score (Score) is categorized into the second category, and displays a message "GOOD SLEEP" in a case in which the sleep score (Score) is categorized into the third category (Step S272). For example, in the case in which the sleep score is categorized into the third category, an evaluation screen indicating the value of the sleep score "Score: 82" and a message "GOOD SLEEP" corresponding to the third category is displayed on the display unit 4 as shown in FIG. 31. Furthermore, CPU 6 uses results of the processes of Steps S5 and S6 to create and display a transition diagram of sleep stages in this sleep. By displaying the sleep score (Score) and a message corresponding to a category of the score, the subject being examined or a user is able to know the overall quality (good or bad) of the sleep. Furthermore, since the transition of sleep stages such as aroused light sleep, or deep sleep is displayed, the result of the evaluation can be used to monitor the conditions of the body of the subject.

CPU 6 then determines whether an operation displaying the next screen is performed (Step S273), and in a case in which such an operation has been performed, the average and the variance values are obtained based on the sleep scores (Score) stored in the memory storage device 9 (Step S274) and displays the sleep score transition screen on display unit 4 (Step S275). For example, as shown in FIG. 32, sleep scores (Score) are assigned to the vertical axis and dates are assigned to the horizontal axis of the bar graph. In a case in which the sleep score (Score) of one day is equal to or less than the addition of the average and the variance computed in Step S274, the bar of the corresponding date of the graph is colored, for example, in a way as shown in FIG. 32 in which the bar corresponding to April 5 is colored. The subject being examined or a user then is able to know the day on which the quality of sleep was bad, and this information can be used to monitor the body conditions of the subject.

CPU 6 then determines whether an operation for displaying the next screen has been made (Step S276), and in a case in which such an operation has been made, CPU 6 ends the determination result display process.

In the above embodiment, the four secondary parameters are derived from the six primary parameters, but the present invention is not limited thereto. For example, n (a natural number satisfying n>2) number of primary parameters may be used to compute m (a natural number satisfying n>m) number of secondary parameters, and the sleep score may be computed based on the m number of secondary parameters. In this case, the primary parameters may be at least three of sleep latency SL, sleep efficiency SE, mid-arousal number WN, deep sleep latency DL, deep sleep time DT, movement number MN, total bed time, out-of-bed latency (time it takes from awakening until getting out of bed), sleep time, total sleep time, mid-arousal period, REM sleep latency, light sleep period, REM sleep period, sleep stage change number, light sleep occurrence number, REM sleep occurrence number, deep sleep occurrence number, REM sleep duration, REM sleep intervals, REM sleep cycle, sleep cycle, the ratio of light sleep in the first and the second half of sleep, the ratio of REM sleep in the first and the second half of sleep, and the ratio of deep sleep in the first half and the second half of sleep. A comprehensive index indicating the degree of the quality of sleep can be appropriately derived from these primary parameters because each of these primary parameters is an index showing a state of sleep.

In the above embodiment, the transition in the sleep score is displayed on display unit 4. CPU 6 may also display the secondary parameters such as efficiency, sleep latency, mid-arousals, and movements, upon which the sleep score is based.

Furthermore, the quality of sleep varies depending on the age and sex of a human subject. For example, the elderly usually have shorter and lighter sleep than children. Therefore, different criteria should be used in evaluating the quality of sleep for the elderly and for children, rather than using the same criteria. Therefore, the first coefficient (eigenvector) used for computing the secondary parameters and the second coefficient (factor loadings) for computing sleep scores may be stored in memory storage device 9 in correspondence with each of plural groups of populations categorized according to the characteristics of the human subject. In this case, when the subject being examined enters the characteristics of the subject by operating operation unit 5, CPU 6 may read from memory storage device 9a pair of the first coefficient and the second coefficient corresponding to the entered characteristics, for use in the computation of the secondary parameters and sleep scores. The characteristics of a human subject thus can be reflected on the sleep scores, thereby enabling more accurate evaluation.

In the present embodiment, a mattress and a condenser microphone are used to detect respiration signals, but the present invention is not limited thereto. For example, a piezoelectric element such as a piezo cable, a capacitance sensor, a film sensor, or a strain gauge may be used to directly detect changes in pressure that take place in accordance with the respiratory movements of a human subject. Alternatively, other known devices may be used, such as a device for measuring respiratory movements by attaching resistance wires on the abdomen or on the chest, and a device for directly measuring respirations by having the subject being examined wear a mask for breath analysis, as long as these devices are capable of detecting respiration signals.

In Step S77 and the subsequent steps in the flowchart of FIG. 13A in which sleep onset period determiner 14 has been described, Conditions D, E, and F are used for determination, and Conditions D, E, and F are tested using the variance of respiration rates, $\sigma^2$, $\sigma\alpha^2$, $\sigma\beta^2$, and $\sigma\gamma^2$. Alternatively, the variance of respiration amplitudes or the variance of respiration cycles may be used.

In Step S138 of the second mid-arousal determination described with reference to the flowchart of FIG. 17, the mid-arousal determination based on respiratory rate is performed based on the condition, "(the average respiratory rate of all the epochs from m=1 to m)≥(the average respiratory rate of all the epochs from n=1 to nmax)*mq". Sleep evaluation device 1 may further be provided with a heart-rate signal detection means (or detector) for detecting indices of the heart rate and a modification means (or modifier) for modifying a sleep stage using the indices of the heart rate. CPU 6 then may use an additional condition, "(the average heart rate of all the epochs from m=1 to m)≥(the average heart rate of all the epochs from n=1 to nmax)*mv", where mv is a constant satisfying mv>1 and may determine that the subject epoch n is an aroused state when the additional condition is satisfied, thereby enabling more precise determination of arousal.

Additionally, the transition in results of determination by sleep evaluation device 1 and the transition in indices of heart rate detected by the heart rate detection means may be used to obtain correlations, which may be used for modifying the results of the determination.

Furthermore, in the above embodiment, the six primary parameters and the four secondary parameters are shown as examples; however, the present invention is not limited thereto, and a sleep score may be computed based on m (a natural number satisfying m>n, where n is a natural number satisfying n≥2) number of secondary parameters that are aggregations of the n number of primary parameters.

What is claimed is:

1. A sleep evaluation system, comprising:
   a biometric signal unit for measuring a state of a human subject, and for outputting a biometric signal; and
   a central processing unit coupled to the biometric signal unit, comprising:
   a primary parameter computation unit for generating, based on the biometric signal, n number of primary parameters indicating a state of sleep, n being a natural number that is at least two;
   a secondary parameter computation unit for generating m number of secondary parameters by multiplying each of the n number of primary parameters by an eigenvector computed based on a correlation matrix, with the eigenvector being a first coefficient, and totalizing results of the multiplications, m being a natural number satisfying n >m and a correlation coefficient of any two of the secondary parameters being smaller than a correlation coefficient of any two of the primary parameters; and
   an evaluation unit for computing a sleep index indicating a quality of sleep based on a result of computation obtained by multiplying each of the secondary parameters by a second coefficient and totalizing results of the multiplications.

2. The system of claim 1, wherein the second coefficient is a factor loading obtained by multiplying the first coefficient by the square root of an eigenvalue.

3. The system of claim 1, wherein the primary parameter computation unit comprises a program code portion for generating , based on the biometric signals, as the n number of primary parameters, at least three of sleep latency, sleep efficiency, mid-arousal number, deep sleep latency, deep sleep time, movement number, total bed time, out-of-bed latency, sleep time, total sleep time, mid-arousal period, REM sleep latency, light sleep period, REM sleep period, sleep stage change number, light sleep occurrence number, REM sleep occurrence number, deep sleep occurrence number, REM sleep duration, REM sleep interval, REM sleep cycle, sleep cycle, the ratio of light sleep in a first and a second half of sleep, the ratio of REM sleep in the first and the second half of the sleep, and the ratio of deep sleep in the first half and the second half of the sleep.

4. The system of claim 3, wherein the primary parameter computation unit comprises a program code portion for generating, as the n number of primary parameters, the sleep latency, the mid-arousal number, the deep sleep latency, the deep sleep time, and the movement number, and wherein the secondary parameter computation unit comprises a program code portion for selecting, as the m number of secondary parameters, four secondary parameters.

5. The system of claim 1, further comprising an inputter for receiving an input of characteristics data of the human subject being examined,
   wherein the primary parameter computation unit stores a plurality of the first coefficients each corresponding to each of plural groups of populations categorized in accordance with the characteristics of human subjects and computes the primary parameters using the first coefficients corresponding to the characteristics received by the inputter, and
   wherein the secondary parameter computation unit stores a plurality of the second coefficients each corresponding to each of plural groups of populations categorized in accordance with the characteristics of human subjects and computes the secondary parameters using the second coefficients corresponding to the characteristics received by the inputter.

6. The system of claim 1, wherein the biometric signal unit comprises a program code portion for measuring the changes in respiration of a human subject and outputs respiration signals as the biometric signals.

7. The system of claim 1, wherein the sleep index computed by the evaluation unit is a sleep score.

8. The system of claim 7, further comprising:
   a display unit for displaying information,
   the central processing unit further comprising:
   a comparison unit for comparing the computed sleep score with at least one reference value bordering plural categories relating to the quality of sleep, to determine one of the categories which the computed sleep score falls in; and
   a first presentation unit for presenting the determined category on the display unit.

9. The system of claim 8,
   wherein the at least one reference value includes at least one of a first reference value showing the addition of the average and the variance of sleep scores of a group of people having sleep disorders and a second reference value showing the addition of the average and the variance of sleep scores of a group of people having normal sleep,
   wherein the categories include at least a first to a third categories, the first category corresponding to a sleep score that is equal to or less than the first reference value, the second category corresponding to a sleep score that exceeds the first reference value and is equal to or less than the second reference value, and the third category corresponding to a sleep score that exceeds the second reference value.

10. The system of claim 1, further comprising:
    a display unit for displaying information; and
    a memory storage device for storing at least two sleep indices computed by the evaluation unit,
    the central processing unit further comprising a second presentation unit for presenting, on the display unit, a sleep index transition including at least two of the at least two of sleep indices.

11. A sleep evaluation system, comprising:
    a biometric signal unit for measuring a state of a human subject, and for outputting a biometric signal; and
    a central processing unit coupled to the biometric signal unit, comprising:
    a primary parameter computation unit for generating, based on the biometric signal, n number of primary parameters indicating a state of sleep, n being a natural number that is at least two;

a secondary parameter computation unit for generating m number of secondary parameters by multiplying each of the n number of primary parameters by an eigenvector computed based on a correlation matrix, with the eigenvector being a first coefficient, and totalizing results of the multiplications, m being a natural number satisfying n≥m and a correlation coefficient of any two of the secondary parameters being smaller than a correlation coefficient of any two of the primary parameters; and an evaluation unit for computing a sleep index indicating a quality of sleep based on a result of computation obtained by multiplying each of the secondary parameters by a second coefficient and totalizing results of the multiplications, wherein the primary parameter computation unit comprises a program code portion for generating, as the n number of primary parameters, sleep latency, mid-arousal number, deep sleep latency, deep sleep time, and movement number, and wherein the secondary parameter computation unit comprises a program code portion for selecting, as the m number of secondary parameters, four secondary parameters.

12. The system of claim 11, further comprising an inputter for receiving an input of characteristics data of the human subject being examined, wherein the primary parameter computation unit stores a plurality of the first coefficients each corresponding to each of plural groups of populations categorized in accordance with the characteristics of human subjects and computes the primary parameters using the first coefficients corresponding to the characteristics received by the inputter, and wherein the secondary parameter computation unit stores a plurality of the second coefficients each corresponding to each of plural groups of populations categorized in accordance with the characteristics of human subjects and computes the secondary parameters using the second coefficients corresponding to the characteristics received by the inputter.

13. A sleep evaluation system, comprising:

a biometric signal unit for measuring a state of a human subject, and for outputting a biometric signal;

a central processing unit coupled to the biometric signal unit, and an inputter for receiving an input of characteristics data of the human subject being examined, the central processing unit comprising:

a primary parameter computation unit for generating, based on the biometric signal, n number of primary parameters indicating a state of sleep, n being a natural number that is at least two;

a secondary parameter computation unit for generating m number of secondary parameters by multiplying each of the n number of primary parameters by an eigenvector computed based on a correlation matrix, with the eigenvector being a first coefficient, and totalizing results of the multiplications, m being a natural number satisfying n≥m and a correlation coefficient of any two of the secondary parameters being smaller than a correlation coefficient of any two of the primary parameters; and an evaluation unit for computing a sleep index indicating a quality of sleep based on a result of computation obtained by multiplying each of the secondary parameters by a second coefficient and totalizing results of the multiplications, wherein the primary parameter computation unit stores a plurality of the first coefficients each corresponding to each of plural groups of populations categorized in accordance with the characteristics of human subjects and computes the primary parameters using the first coefficients corresponding to the characteristics received by the inputter, and wherein the secondary parameter computation unit stores a plurality of the second coefficients each corresponding to each of plural groups of populations categorized in accordance with the characteristics of human subjects and computes the secondary parameters using the second coefficients corresponding to the characteristics received by the inputter.

* * * * *